United States Patent
Axelsson et al.

(10) Patent No.: US 8,475,768 B2
(45) Date of Patent: Jul. 2, 2013

(54) PARAMAGNETIC CHELATES THEREOF AND THEIR USE AS CONTRAST AGENTS IN MAGNETIC RESONANCE IMAGING (MRI)

(75) Inventors: Oskar Axelsson, Linkoping (SE); Harry John Wadsworth, Amersham (GB); Ian Martin Newington, Amersham (GB); Dennis O'Shea, Amersham (GB)

(73) Assignee: GE Healthcare AS, Oslo (NO)

( * ) Notice: Subject to any disclaimer, the term of this patent is extended or adjusted under 35 U.S.C. 154(b) by 250 days.

(21) Appl. No.: 12/672,113

(22) PCT Filed: Aug. 12, 2008

(86) PCT No.: PCT/EP2008/060570
§ 371 (c)(1),
(2), (4) Date: Jan. 25, 2011

(87) PCT Pub. No.: WO2009/021947
PCT Pub. Date: Feb. 19, 2009

(65) Prior Publication Data
US 2011/0110865 A1    May 12, 2011

(30) Foreign Application Priority Data

Aug. 13, 2007 (NO) .................................... 20074166

(51) Int. Cl.
*A61B 5/055* (2006.01)
*C08G 18/62* (2006.01)
*C07D 213/62* (2006.01)

(52) U.S. Cl.
USPC ............................ 424/9.32; 525/451; 546/261

(58) Field of Classification Search
USPC ....................................................... 424/9.32
See application file for complete search history.

(56) References Cited

U.S. PATENT DOCUMENTS

2003/0095922 A1*  5/2003  Raymond et al. ............ 424/1.69

FOREIGN PATENT DOCUMENTS

| WO | 97/00245 | 1/1997 |
| WO | 2008/085064 | 7/2008 |

OTHER PUBLICATIONS

Zhou et al. (2005). "High Affinity iron(III) scavenging by a novel hexadentate 3-hydroxypyridin-4-one-based dendrimer: Synthesis and characterization". Bioorganic & Medicinal Chemistry Letters, 15: 5007-5011.*

Puerta, et.al. "Tis(Pyrone) Chelates of Gd(III) As High Solubility MRI-CA" Journal of the American Chemical Society, Am. Ch. Soc. Washington, DC. vol. 128, Jan. 2, 2006, pp. 222-223.

Imbert, D. et.al. "Synthesis and Iron(III) Complexing Ability of CacCAM, A New Analog of Enterobactin Prossessing a Free Carboxylic Anchor Arm. Comparative Studies With TRENCAM" New Journal of Chemistry, CNRS-Gauthier-Villars, Montrouge, FR. vol. 24, Jan. 1, 2000, pp. 281-288.

Caravan P, et.al. "Gadolinium (III) Chelates As MRI Contrast Agents: Structure, Dynamics and Applications" Chemical Reviews, ACS, Wasington, DC. vol. 99, No. 9, Sep. 1, 1999, pp. 2293-2352.

* cited by examiner

*Primary Examiner* — Robert T Crow
*Assistant Examiner* — Doan Phan

(57) ABSTRACT

The present invention relates to chelators, in particular to chelators which are capable of forming complexes, i.e. paramagnetic chelates, with paramagnetic metal ions. The invention also relates to said paramagnetic chelates, said paramagnetic chelates linked to other molecules and their use as contrast agents in magnetic resonance imaging (MRI).

23 Claims, No Drawings

PARAMAGNETIC CHELATES THEREOF AND THEIR USE AS CONTRAST AGENTS IN MAGNETIC RESONANCE IMAGING (MRI)

This application is a filing under 35 U.S.C. 371 of international application number PCT/EP2008/060570, filed Aug. 12, 2008, which claims priority to Norwegian application number 20074166 filed Aug. 13, 2007, the entire disclosure of which is hereby incorporated by reference.

The present invention relates to chelators, in particular to chelators which are capable of forming complexes, i.e. paramagnetic chelates, with paramagnetic metal ions. The invention also relates to said paramagnetic chelates, said paramagnetic chelates linked to other molecules and their use as contrast agents in magnetic resonance imaging (MRI).

MRI is a medical imaging technique in which areas of the body are visualised via the nuclei of selected atoms, especially hydrogen nuclei. The MRI signal depends upon the environment surrounding the visualised nuclei and their longitudinal and transverse relaxation times, $T_1$ and $T_2$. Thus, in the case when the visualised nucleus is a proton, the MRI signal intensity will depend upon factors such as proton density and the chemical environment of the protons. Contrast agents are often used in MRI in order to improve the imaging contrast. They work by effecting the $T_1$, $T_2$ and/or $T_2^*$ relaxation time and thereby influence the contrast in the images.

Several types of contrast agents have been used in MRI. Blood pool MR contrast agents, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours which are a result of tumour angiogenesis.

Water-soluble paramagnetic chelates, i.e. complexes of a chelator and a paramagnetic metal ion—for instance gadolinium chelates like Omniscan™ (GE Healthcare)—are widely used MR contrast agents. Because of their low molecular weight they rapidly distribute into the extracellular space (i.e. the blood and the interstitium) when administered into the vasculature. They are also cleared relatively rapidly from the body.

The problem with the in vivo use of paramagnetic metal ions in a MRI contrast agent is their toxicity and therefore they are provided as complexes with chelators which are more stable and less toxic.

For a paramagnetic chelate to be useful as a contrast agent in MRI, it is necessary for it to have certain properties. Firstly, it must have high stability because it is important that the complex does not break down in situ and release toxic paramagnetic metal ions into the body.

Secondly, in order for it to be a potent MRI contrast agent, a paramagnetic chelate must have high relaxivity. The relaxivity of a MRI contrast agent refers to the amount of increase in signal intensity (i.e. decrease in $T_1$) that occurs per mole of metal ions. Relaxivity is dependent upon the water exchange kinetics of the paramagnetic chelate.

The solubility of the paramagnetic chelate in water is also an important factor when they are used as contrast agents for MRI because they are administered to patients in relatively large doses. A highly water-soluble paramagnetic chelate requires a lower injection volume, is thus easier to administer to a patient and causes less discomfort.

U.S. Pat. No. 5,624,901 and U.S. Pat. No. 5,892,029 both describe a class of chelators based on 1-hydroxy-2-pyridinone and 3-hydroxy-2-pyridinone moieties which have a substituted carbamoyl group adjacent the hydroxyl or oxo groups of the ring. The compounds are said to be useful as actinide sequestering agents for in vivo use because of their ability to form complexes with actinides. However, it does not refer directly to the complexes which are formed or to any possibility of using them as MRI contrast agents.

U.S. Pat. No. 4,666,927 also relates to hydroxypyridinones. The preferred compounds have an oxo group in either the 2- or the 4-position and a hydroxyl group in the 1- or 3-position. The only other ring substituents are alkyl groups and the compounds are said to be useful as agents for the treatment of general iron overload.

US-A-2003/0095922 relates to complexes formed between gadolinium (III) ions and an organic chelator. The chelator is said to be based on a pyridinone, pyrimidinone or pyridazinone ring system. The exemplified pyridinone compounds are all 3-hydroxy-2-pyridinones with a carbamoyl group in the 4-position of the ring. The compounds are said to be useful as MRI contrast agents and to have high solubility and low toxicity.

D. T. Puerta et al, J. Am. Chem. Soc. Vol. 128, No. 7, 2006, 2222-2223 describes gadolinium chelates of 3-hydroxy-4-pyrones, which are high relaxivity MRI contrast agents with moderate solubility.

US-A-2006/0292079 describes bifunctional chelates based on the chelators 3-hydroxypyridine-2-one, and 5-hydroxy-pyrimidin-4-one. The chelates containing gadolinium (III) are used as MRI contrast agents.

The present inventors have developed improved chelators and paramagnetic chelates thereof which can be used as MR contrast agents.

Therefore, in a first aspect of the present invention there is provided a compound of formula (I):

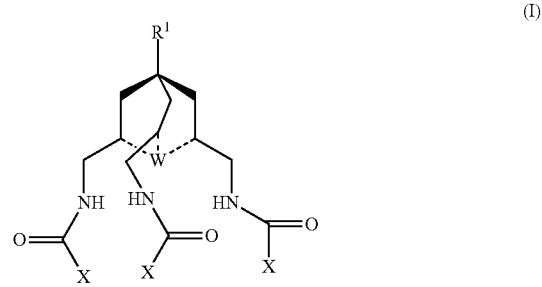

wherein $R^1$ is H, $NO_2$, $NH_2$ or $NHC(=O)R^2$, wherein $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$ wherein n is 0 to 6 and m is 1 to 6;

W and the bonds represented as dotted lines are present or absent and when present, W is N; and X is a chelator moiety consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions.

The term "chelator" denotes a chemical entity that binds (complexes) a metal ion to form a chelate. If the metal ion is a paramagnetic metal ion, the chemical entity, i.e. complex, formed by said paramagnetic metal ion and said chelator is denoted a paramagnetic chelate. Compounds of formula (I) are chelators since they bind to metal ions via the chelator moiety X.

A preferred embodiment of a compound of formula (I) is a compound of formula (II), a paramagnetic chelate, comprising a compound of formula (I) and a paramagnetic metal ion M:

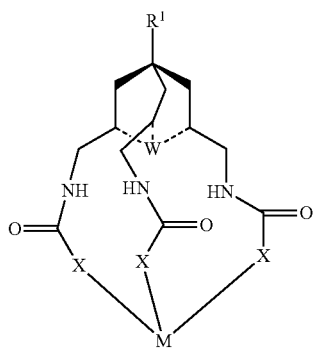
(II)

wherein
$R^1$, W and X are as defined above and M is a paramagnetic metal ion.

In the present specification, the term "alkyl" by itself or as part of another substituent refers to a fully saturated straight or branched hydrocarbon chain group having the number of carbon atoms designated. Thus, $C_1$-$C_6$-alkyl means a fully saturated straight or branched hydrocarbon chain group having 1 to 6 carbon atoms and examples of $C_1$-$C_6$-alkyl are methyl, ethyl, n-propyl, isopropyl, n-butyl, isobutyl, t-butyl, n-pentyl, iso-pentyl and n-hexyl.

The term "aryl" by itself or as a part of another substituent refers to an aromatic ring system group consisting of up to three fused or covalently linked rings having the number of carbon atoms designated. Thus, $C_6$-$C_{10}$-aryl refers to an aromatic ring system group consisting of up to three fused or covalently linked rings and having 6 to 10 carbon atoms and examples of $C_6$-$C_{10}$-aryl are phenyl or naphthyl.

The term "arylalkyl" refers to an aryl-substituted alkyl group wherein said aryl and alkyl group are as defined above and wherein said arylalkyl group has the number of carbon atoms designated. Thus, $C_7$-$C_{13}$-arylalkyl refers to an aryl-substituted alkyl group having 7 to 13 carbon atoms and examples of $C_7$-$C_{13}$-arylalkyl are benzyl or phenethyl.

In the present specification the term "paramagnetic metal ion" is a an ion selected from ions of transition and lanthanide metals, i.e. metals of atomic numbers 21 to 29, 42 to 44 or 57 to 71.

Compounds of formula (I) and (II) may exist in either solvated or unsolvated forms and both are encompassed within the scope of the present invention. The present invention also encompasses all solid forms of the compounds, including amorphous and all crystalline forms.

Certain compounds of formula (I) and (II) may exist in different isomeric forms and the present invention is intended to encompass all isomers including enantiomers, diastereoisomers and geometrical isomers as well as racemates.

Compounds of formula (I) and (II) comprise a chelator moiety, i.e. group X. Preferred groups X include groups derived from hydroxypyrones, dihydroxypyridines, hydroxypyrimidones, hydroxypyridones hydroxypyridinones and dihydroxyphenols, any of which may be substituted as described above.

Groups X derived from hydroxypyridones and hydroxypyrimidinones are disclosed in US 2003/0095922.

Groups X derived from hydroxypyridinones which are capable of forming chelates with paramagnetic metal ions are also disclosed in U.S. Pat. No. 4,698,431, U.S. Pat. No. 4,666,927, U.S. Pat. No. 5,624,901 and our own earlier application number PCT/NO2008/000012.

Preferred groups X are of formula (IIIa) to (IIIg)

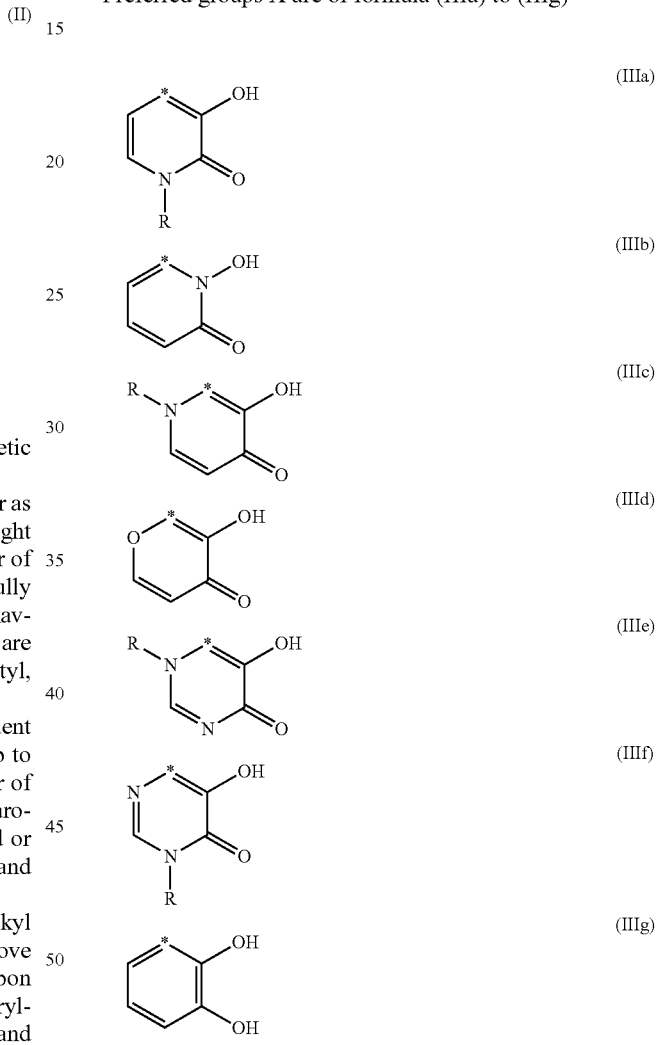

wherein R is as defined in formula (I) and (II) and * indicates the point of attachment of the group X to the remainder of the compound of formula (I) and (II).

In compounds of formula (II) the chelator moieties X form a complex, i.e. paramagnetic chelate with a paramagnetic metal ion M. In a preferred embodiment, M is a paramagnetic metal ion of Mn, Fe, La, Co, Ni, Eu, Gd, Dy, Tm and Yb, particularly preferred a paramagnetic metal ion of Mn, Fe, La, Eu, Gd and Dy. Most preferably, M is selected from $Gd^{3+}$, $Mn^{2+}$, $Fe^{3-}$, $Dy^{3+}$ and $Eu^{3+}$ with $Gd^{3+}$ being the most preferred paramagnetic metal ion M.

The chelator moieties X in compounds of formula (I) and (II) may be substituted by up to three additional substituents, R, where each R is independently a hydrophilic group which renders the compound of formula (II) soluble in aqueous solutions.

Examples of preferred compounds of formula (I) and (II) are shown below as general formulae (Ia), (Ib), (IIa) and (IIb):

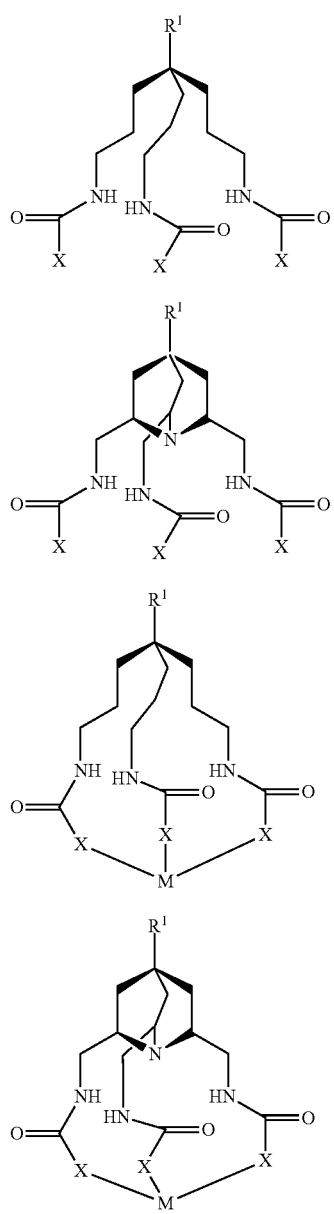

wherein $R^1$, X and M are as defined above.

Preferred hydrophilic groups R are groups comprising ester groups, amide groups or amino groups which are optionally further substituted by one or more straight chain or branched $C_1$-$C_{10}$-alkyl groups, preferably $C_1$-$C_5$-alkyl groups where said alkyl groups also may have one or more $CH_2$- or CH-moieties replaced by oxygen or nitrogen atoms. The aforementioned preferred hydrophilic groups R may further contain one or more groups selected from hydroxy, amino, oxo, carboxy, amide group, ester group, oxo-substituted sulphur and oxo-substituted phosphorus atoms. The aforementioned straight chain or branched $C_1$-$C_{10}$-alkyl groups, preferably $C_1$-$C_5$-alkyl groups, preferably contain 1 to 6 hydroxyl groups and more preferably 1 to 3 hydroxyl groups.

Particularly preferred hydrophilic groups R according to the embodiment described above are the following groups R which are attached to a carbon atom in the chelator moiety X and wherein said chelator moiety X is substituted by only 1 of said following groups R. * indicates the point of attachment of the group R to X:

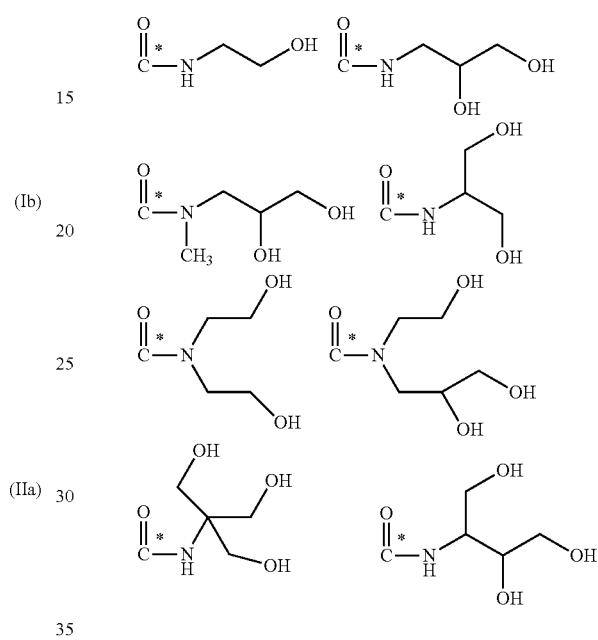

Further preferred hydrophilic groups R are preferably attached to heteroatoms in the chelator moiety X, more preferably attached to nitrogen atoms in the chelator moiety X and such hydrophilic groups R are straight chain or branched $C_1$-$C_{10}$-alkyl groups, preferably $C_1$-$C_5$-alkyl groups which are substituted by 1 to 6 hydroxyl groups and more preferably by 2 to 5 hydroxyl groups and/or which are substituted by one or more alkyloxy groups, preferably $C_1$-$C_3$-alkyloxy groups like methyloxy, ethyloxy and propyloxy groups.

Particularly preferred hydrophilic groups R according to the embodiment described above are the following and * indicates the point of attachment of the group R to X:

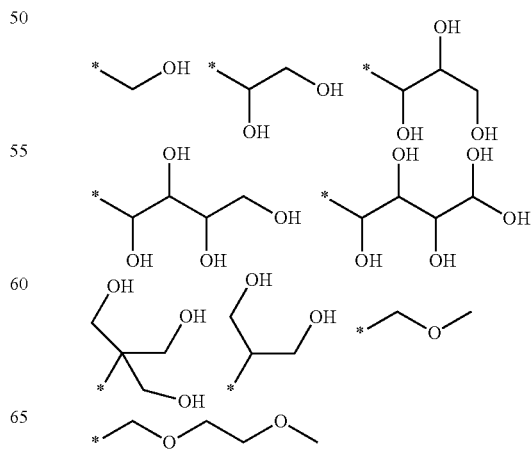

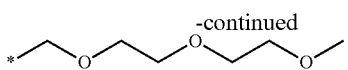

Further preferred hydrophilic groups R are preferably attached to heteroatoms in the chelator moiety X, more preferably attached to nitrogen atoms in the chelator moiety X and such hydrophilic groups R are groups that comprise up to 3 ethylene oxide units.

Particularly preferred hydrophilic groups R according to the embodiment described above are the following and * indicates the point of attachment of the group R to X:

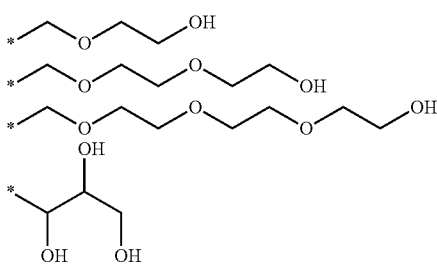

Compounds of formula (I) are chelators since they contain chelating moieties X and they can thus be used to chelate metal ions, preferably paramagnetic metal ions. They may or may not be linked via the $R^1$-group to other molecules like natural or synthetic peptides, peptidomimetics, polypeptides, proteins, antibodies, natural or synthetic polymers or dendrimers, nanoparticles or lipophilic compounds.

Compounds of formula (II) can be used as MR contrast agents and may or may not be linked via the $R^1$-group to other molecules such as natural or synthetic peptides, peptidomimetics, polypeptides, proteins or antibodies. By linking compounds of formula (II) to these molecules, targeted MR contrast agents may be obtained if the for instance peptide or protein is a vector which binds to a target like a receptor or cell surface marker. Further, compounds of formula (II) may be linked via the $R^1$-group to polymeric moieties such as natural or synthetic polymers or dendrimers. Such a linking gives compounds of formula (II) a further reduced molecular mobility and therefore increase its relaxivity at high field strengths used in modern MRI scanners. In another embodiment compounds of formula (II) may be linked to lipophilic compounds and the resulting amphiphilic compounds may be dispersed. Such dispersions may be used as MR contrast agent for tumour imaging. In yet another embodiment the compounds of formula (II) may be linked to nanoparticles. Again such a linking gives compounds of formula (II) a further reduced molecular mobility and therefore increases their relaxivity.

Therefore, in a second aspect of the invention there is provided a compound of formula (I) and (II) as defined above linked to another molecule via the $R^1$-group. In a preferred embodiment, said another molecule is a natural or synthetic peptide, a peptidomimetic, a polypeptide, a protein, an antibody, a natural or synthetic polymer, a dendrimer, a nanoparticle or a lipophilic compound.

The term "linked via the $R^1$-group" means that in one embodiment the compounds of formula (I) and (II) are directly linked to another molecule as described above via the $R^1$-group as defined earlier. It is apparent for the skilled person that certain $R^1$-groups as defined, i.e. a $NH_2$-group, are functional groups which can be converted to numerous other functional groups by methods known in the art. Thus the term "linked via the $R^1$-group" also includes embodiments wherein the $R^1$-group as defined earlier is first converted into another functional group before the compounds of formula (I) and (II) are then linked to another molecule via said now converted $R^1$-group.

If compounds of formula (I) or (II) are linked to other molecules like natural or synthetic peptides, peptidomimetics, polypeptides, proteins, antibodies, natural or synthetic polymers or dendrimers, $R^1$ is preferably $NH_2$ or $NHC(=O)R^2$ wherein $R^2$ is $(CH_2)_n-(C_6H_4)-NCS$, $(CH_2)_m-C\equiv CH$ or $(CH_2)_m-N_3$ wherein n is 0 to 6 and m is 1 to 6. In one embodiment, the $R^1$-group is $NH_2$ which is a functional group which may be converted to numerous other functional groups by methods known in the art. In order to link a compound of formula (I) or (II) wherein the $R^1$-group is a $NH_2$-group to another molecule said linking may either be carried out by reacting the $NH_2$-group of the compound of formula (I) or (II) with a suitable reactive group on said molecule, e.g. reactive groups like acid chlorides or acid anhydrides. Alternatively, the $NH_2$-group may be converted in a first step to another functional group before compounds of formula (I) or (II) are linked to said other molecule.

If compounds of formula (I) or (II) are linked to other larger molecules like for instance polypeptides, proteins, antibodies or synthetic or natural polymers or dendrimers, $R^1$ is preferably $NHC(=O)R^2$ wherein $R^2$ is $(CH_2)_n-(C_6H_4)-NCS$, $(CH_2)_m-C\equiv CH$ or $(CH_2)_m-N_3$ wherein n is 0 to 6 and m is 1 to 6. By using compounds of formula (I) or (II) with the aforementioned groups $R^1$, it is possible to use "click chemistry" (e.g. described by M. Malkoch et al., Macromolecules 38(9), 2005, 3663-3678 or P. Wu et al., Chem. Commun. 46, 2005, 5775-5777). Click chemistry allows linking single or preferably multiple compounds of formula (I) or (II) to a larger molecule in a very high yielding reaction. Further, the linking reaction can be carried out in conditions that dissolve the reactants such as aqueous conditions.

In a preferred embodiment, $R^1$ is preferably $NHC(=O)R^2$ wherein $R^2$ is as follows and * denotes the attachment point of $R^2$ to the carbon atom of group $NHC(=O)R^2$:

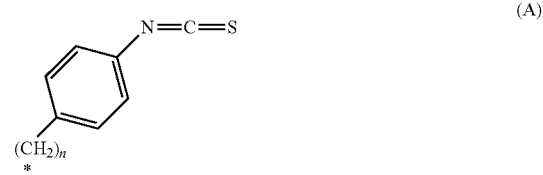

(A)

(B)

(C)

Compounds of formula (I) or (II) wherein $R^1$ is $NHC(=O)R^2$ and $R^2$ is (A), i.e. $(CH_2)_n-(C_6H_4)-NCS$, can be reacted with another (large) molecule comprising amino groups $-NH_2$ under formation of thiourea bonds ($-NH-C(=S)-NH-$).

Compounds of formula (I) or (II) wherein $R^1$ is $NHC(=O)R^2$ and $R^2$ is (B), i.e. $(CH_2)_m-C\equiv CH$, can be reacted with another (large) molecule comprising azido groups —N₃ under formation of 1, 2, 3 triazole rings.

Compounds of formula (I) or (II) wherein $R^1$ is NHC(=O)$R^2$ and $R^2$ is (C), i.e. $(CH_2)_m$—$N_3$, can be reacted with another (large) molecule comprising ethynyl groups —C≡CH under formation of 1, 2, 3 triazole rings.

If the compounds of formula (I) or (II) are not linked to other molecules, $R^1$ is preferably H, NO₂, or NHC(=O)$R^2$, wherein $R^2$ is $C_1$-$C_6$-alkyl, $C_6$-$C_{15}$-aryl, $C_7$-$C_{22}$-arylalkyl, O—$C_1$-$C_6$-alkyl or O—$C_7$-$C_{22}$-arylalkyl. In a preferred embodiment $R^1$ is H or NHC(=O)$R^2$, wherein $R^2$ is $C_1$-$C_6$-alkyl or O—$C_1$-$C_6$-alkyl, more preferably H or NHC(=O)$R^2$, wherein $R^2$ is $C_1$-$C_4$-alkyl or O—$C_1$-$C_4$-alkyl, like for instance $CH_3$, $C(CH_3)_3$, $OCH_3$ or $OC(CH_3)_3$.

In another embodiment a compounds of formula (I) or (II) is linked to a lipophilic compound to result in an amphiphilic compound of formula (I) or (II). Suitable lipophilic compounds are known in the art and contain a functional group that reacts with the $R^1$-group, preferably the $NH_2$-group, present in compounds of formula (I) and (II) and a lipophilic residue selected from the group of higher alkyl or higher alkenyl, preferably $C_8$-$C_{20}$-alkyl or $C_8$-$C_{20}$-alkenyl, arylalkyl or alkylaryl, cholesterol derivatives or bile salts. Suitable lipophilic compounds are for instance fatty acid chlorides like oleoyl chloride or stearyl chloride.

The resulting amphiphilic compound of formula (I) can then be reacted with for instance a salt containing a paramagnetic metal ion like for instance Gd(III)Cl₃ to result in a an amphiphilic compound of formula (II), hereinafter denoted "amphiphilic chelate". The amphiphilic chelate can then be dispersed, optionally in combination with lipids or surfactants or a carrier oil phase to obtain a preferably monodisperse formulation of a chosen size, preferably a micellar size. Techniques for obtaining such dispersions are known in the art. Alternatively, the resulting amphiphilic compound of formula (I) is dispersed, optionally in combination with lipids or surfactants or a carrier oil phase to obtain a preferably monodisperse formulation of a chosen size, preferably a micellar size and the formulation is then reacted with for instance a salt containing a paramagnetic metal ion like for instance Gd(III)Cl₃ to result in a dispersed amphiphilic chelate, i.e. dispersed amphiphilic compound of formula (II).

As described earlier, capillary walls in tumours show permeability abnormalities, e.g. "leakiness" which is a result of tumour angiogenesis. By tailoring the size of the dispersed amphiphilic chelates in such a way that the dispersed amphiphilic chelate can pass through these leaky capillary walls into the tumour tissue (e.g. micellar size) it should be possible to obtain an MR contrast agent for tumour imaging.

In another embodiment, other contrast/imaging agents may be incorporated into such dispersed amphiphilic chelates, such as X-ray agents or air so that a combined MRI-X-ray or MRI-ultrasound agent would result.

Therefore, in a third aspect of the invention there is provided compounds of formula (I) or (II) which are linked via an amide bond to a lipophilic compound.

Said compounds of formula (I) or (II) which are linked via an amide bond to a lipophilic compound may be obtained by reacting compounds of formula (I) or (II) wherein the $R^1$-group is a $NH_2$-group, to a lipophilic compound comprising groups Y—C(=O)—* wherein Y is a leaving group, preferably a halide, a mixed anhydride, an activated ester such as O-succinimide or an activated amine such as imidazolide and * indicates the attachment point of said group Y—C(=O)— to said lipophilic compound.

In yet another embodiment, compounds of formula (I) or (II) are linked via the $R^1$-group, preferably via a $NH_2$-group, to a nanoparticle surface. Preferred nanoparticles are metal oxide nanoparticles, gold nanoparticles, silver nanoparticles, silica nanoparticles, zinc nanoparticles or titanium nanoparticles. The choice of functional group, i.e. the $R^1$-group depends on the type of nanoparticle the compound of formula (I) and (II) is linked to. In a preferred embodiment, the nanoparticle is a gold nanoparticle and the $R^1$-group, preferably a $NH_2$-group, present in compounds of formula (I) and (II) is derivatised in such a way that it contains a thiol moiety and said thiol moiety can be used to link said compounds of formula (I) and (II) to the surface of a gold nanoparticle. In another embodiment, the $R^1$-group, preferably a $NH_2$-group, present in compounds of formula (I) and (II) is derivatised in such a way that it contains a trialkyloxysilane moiety and trialkyloxysilane can be used to link said compounds of formula (I) and (II) to the surface of a metal oxide nanoparticle. By linking compounds of formula (II) to a nanoparticle, multiple molecules of compounds of formula (II) are held rigidly relative to one another and this, together with the number of molecules of compounds of formula (II) per nanoparticle would ensure high relaxivity. In another embodiment, the nanoparticle itself has a function other than just being a carrier. In particular, the nanoparticle may have fluorescent properties thus resulting in a compound which is a combined MR—optical imaging agent.

Therefore, in a forth aspect of the invention there is provided compounds of formula (I) and (II) as defined above linked via the $R^1$-group, preferably via a $NH_2$-group or derivatised $NH_2$-group to a nanoparticle surface. In a preferred embodiment, the nanoparticle is a metal oxide nanoparticle, a gold nanoparticle, a silver nanoparticle, a silica nanoparticle, a zinc nanoparticle or a titanium nanoparticle.

For the synthesis of compounds of formula (I) compounds of formula (IVa) and (IVb) are useful starting materials:

(IVa)

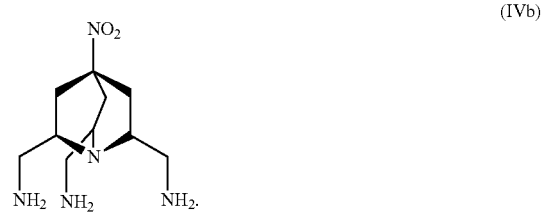

(IVb)

The compound of formula (IVa) can be prepared from tris-(2-cyanoethyl)nitromethane, a commercially available compound, which is reduced with BH₃/THF complex as described by S. Lebreton et al., Tetrahedron 59 (2003), 3945-3953.

The compound of formula (IVb) can be prepared as shown in reaction scheme 1:

Reaction scheme 1

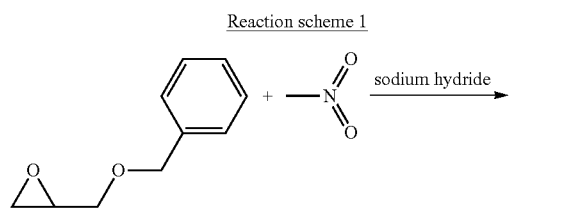

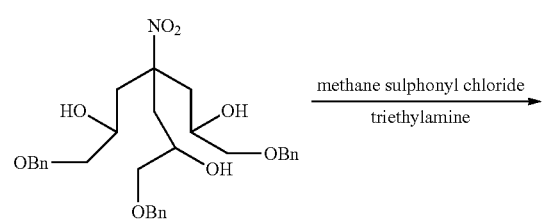

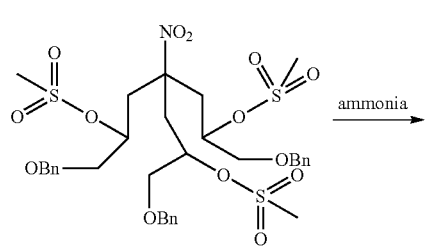

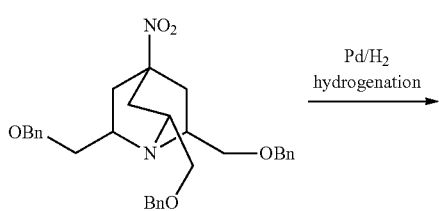

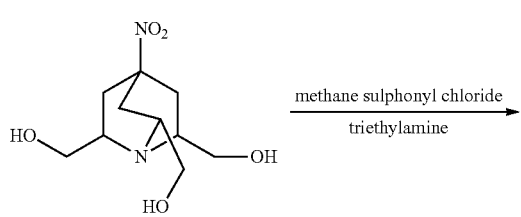

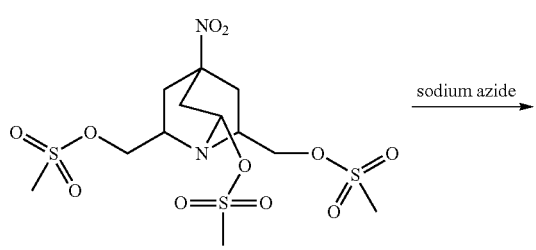

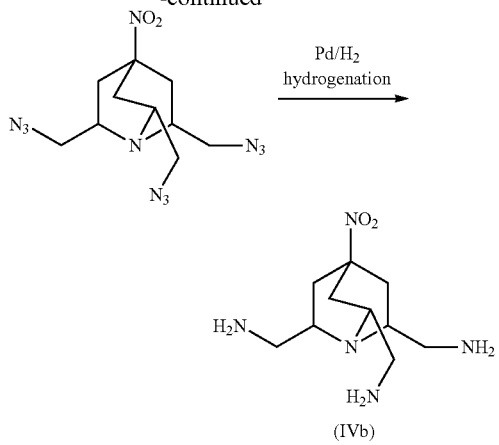

Excess benzyl glycidyl ether is reacted with nitromethane with base such as potassium tert.-butoxide in a solvent such as THF. The resulting triol is treated with methane sulphonyl chloride and a base such as triethylamine or pyridine in a solvent such as dichloromethane. The trimethane sulphonate is then reacted with ammonia in a solvent such as THF. The benzyl protecting groups are then removed by hydrogenation with palladium on charcoal to give the nitro triol. The triol functions are then converted to leaving groups by reaction with an activating group such as methane sulphonyl chloride in a solvent such as THF or dichloromethane. The leaving groups are then reacted with sodium azide to displace them and give the triazide. The azido groups can then be hydrogenated over palladium on charcoal to give the compound of formula (IVb) in a solvent such as methanol.

For the synthesis of compounds of formula (I) wherein $R^1$ is H, compound of formula (IVc) is a useful starting material:

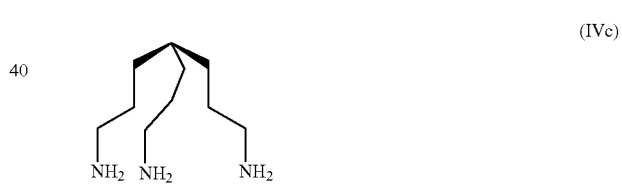

The compound of formula (IVc) can be prepared from the compound of formula (IVa) described above by its treatment with BOC anhydride to protect the three amine groups. The resulting protected compound is then treated with 2,2'azobis (2-methylpropionitrile) and tri-butyl tin hydride in benzene at reflux to remove the nitro group in a radical reaction. The BOC protecting groups can then be removed with trifluoro acetic acid. The reaction is shown in reaction scheme 2:

Reaction scheme 2.

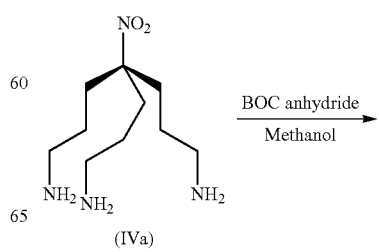

-continued

[Structure: tri-boc protected triamine with NO₂ group, with AIBN/Tributyl tin hydride arrow]

[Structure: tri-boc protected triamine, with TFA arrow]

[Structure (IVc): triamine with three NH₂ groups]

Compounds of formula (IVa), (IVb) and (IVc) are then reacted with a compound of formula (V) comprising the chelating moiety X in a protected form and a leaving group:

$$X^Z-C(=O)Y \qquad (V)$$

wherein $X^Z$ is X as defined before wherein the hydroxyl groups which are bound to X are protected; and Y is a leaving group, preferably a halide, a mixed anhydride, an activated ester such as O-succinimide or an activated amide such as imidazolide.

The product obtained may then be reduced (if $R^1$ is $NO_2$) and is deprotected to obtain compounds of formula (I) wherein $R^1$ is $NH_2$ or H.

Thus, another aspect of the invention is a method for producing a compound of formula (I) wherein $R^1$ is $NH_2$ or H by a) reacting a compound of formula (IVa), (IVb) or (IVc)

[Structure (IVa): NO₂ with three NH₂ arms]

[Structure (IVb): bicyclic with NO₂ and three NH₂ arms]

[Structure (IVc): three NH₂ arms]

with a compound of formula (V)

$$X^Z-C(=O)Y \qquad (V)$$

wherein $X^Z$ is X as defined earlier and wherein the hydroxyl groups which are bound to X are protected; and Y is a leaving group;

b) if a compound of formula (I) wherein $R^1$ is $NH_2$ is the desired product, reducing the nitro group to obtain an amino group; and c) removing the hydroxyl protecting groups of $X^Z$.

The hydroxyl group(s) present in X, i.e. attached to the ring system need to be protected. Suitable protecting groups for hydroxyl groups are well known in the art and are for instance described in "Protecting Groups in Organic Synthesis", Theodora W. Greene and Peter G. M. Wuts, published by John Wiley & Sons Inc. Examples of suitable groups of protecting groups for hydroxyl groups include tem-butyl groups or benzyl, with benzyl being preferred.

If X contains one or more substituents R, hydroxyl groups present in R may or may not be protected. If R comprise other reactive groups than the aforementioned hydroxyl groups, e.g. such as amine groups, such groups need to be protected as well. Again suitable protecting groups are well known in the art.

The reaction of compounds of formula (IVa), (IVb) or (IVc) with compounds of formula (V) is preferably conducted in organic solvent(s) such as dichloromethane or tetrahydrofuran (THF) under anhydrous conditions but for some reagents, an aqueous solution may be used. The reaction of compounds of formula (IVa), (IVb) or (IVc) with compounds of formula (V) give compounds of formula (VIa), (VIb) or (VIc), respectively.

The reaction is illustrated in reaction scheme 3:

Reaction scheme 3.

[Structure (IVa): NO₂ with three NH₂ arms] + [X²–C(=O)–Y structure] →

[Product structure: NO₂ with three NH–C(=O)–X^Z arms]

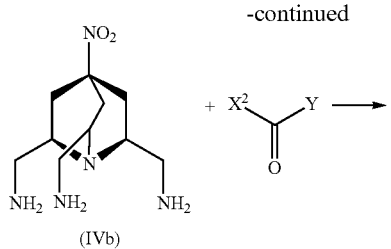

(IVb)

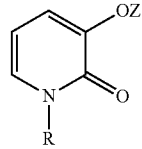

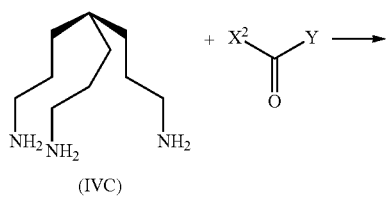

(VIb)

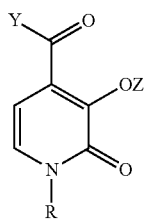

(IVC)

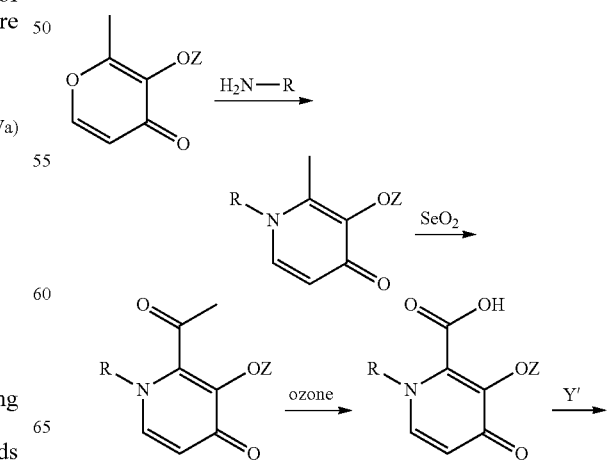

(VIc)

Compounds of formula (V) are also known and may be prepared by known methods. For example, compounds of formula (V) in which X is a group of formula (IIIa) are designated compounds of formula (Va):

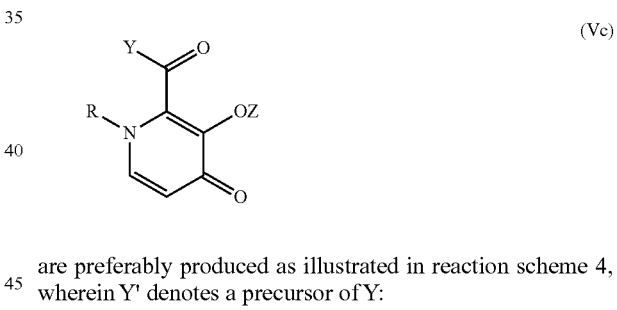

(Va)

wherein R and Y are as defined above and Z is a protecting group for OH as described above.

Compounds (Va) may be prepared by reacting compounds of formula (VII) which are well known in the art:

(VII)

wherein R and Z are as defined above, with carbon dioxide in the presence of a base. A suitable method for this reaction is set out in U.S. Pat. No. 5,624,901.

Other compounds of formula (V) which have a different X group, for example an X group of formula (IIIb), (IIIe), (IIIf) and (IIIg) can be prepared by methods similar to those above or methods known to those skilled in the art and set out in, for example US-A-2003/0095922, Z. Liu et al., Bioorg. Med. Chem. 9 (2001), 563-573, S. Piyamongkol et al., Tetrahedron Letters 46 (2005), 1333-1336, V. Pierre et al., J. Am. Chem. Soc. 2006, 128, 5344-5345, J. Xu et al., J. Am. Chem. Soc. 1995, 117, 7245-7246, D. Doble et al., J. Am. Chem. Soc. 2001, 123, 10758-10759, M. Allen et al., J. Am. Chem. Soc. 2006, 128, 6534-6535, M. Seitz et al., Inorg. Chem. 2007, 46, 351-353, K. Clarke Jurchen et al., Inorg. Chem. 2006, 45, 1078-1090, B. O'Sullivan et al., Inorg. Chem. 2003, 42, 2577-2583, D. Doble et al., Inorg. Chem. 2003, 42, 4930-4937, S. Dhungana et al., Inorg. Chem. 2001, 40, 7079-7086, A. Johnson et al., Inorg. Chem. 2000, 39, 2652-2660, S. Cohen et al., Inorg. Chem. 2000, 39, 4339-4346.

Compounds of formula (Vc) which have an X group of formula (IIIc):

(Vc)

are preferably produced as illustrated in reaction scheme 4, wherein Y' denotes a precursor of Y:

Reaction scheme 4.

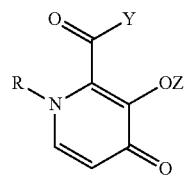

By deprotecting compounds of formula (VIa) and (VIb), compounds of formula (I) are obtained wherein $R^1$ is $NO_2$. By reducing compounds of formula (VIa) and (VIb) and deprotecting the reaction product from that reduction reaction, compounds of formula (I) are obtained wherein $R^1$ is $NH_2$. By deprotecting compounds of formula (VIc), compounds of formula (I) are obtained wherein $R^1$ is H.

Compounds of formula (VIa) and (VIb) are suitable starting compounds for the synthesis of compounds of formula (I), wherein $R^1$ is $NH_2$ or $NHC(=O)R^2$, wherein $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$ wherein n is 0 to 6 and m is 1 to 6.

Thus, in another aspect the invention provides a method for producing a compound of formula (I) wherein $R^1$ is NHC(=O)$R^2$, wherein $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_m$—C≡CH or $(CH_2)_m$—$N_3$ wherein m is 1 to 6 by a) reacting a compound of formula (IVa) or (IVb)

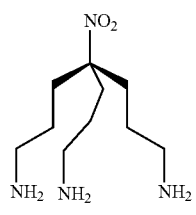

(IVa)

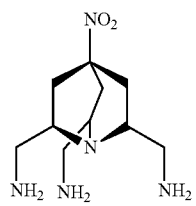

(IVb)

with a compound of formula (V)

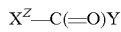 (V)

wherein $X^Z$ is X as defined earlier and wherein the hydroxyl groups which are bound to X are protected; and Y is a leaving group;

b) reducing the nitro group to obtain an amino group;

c) reacting the product obtained with a compound of formula (IX)

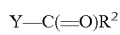 (IX)

wherein Y and $R^2$ are as defined above; and d) removing the hydroxyl protecting groups of $X^Z$.

Thus, in another aspect the invention provides a method for producing a compound of formula (I) wherein $R^1$ is NHC(=O)$R^2$ and $R^2$ is $(CH_2)_n$—$(C_6H_4)$—NCS wherein n is 0 to 6 by a) reacting a compound of formula (IVa) or (IVb)

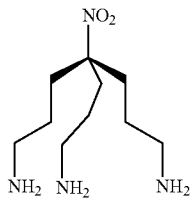

(IVa)

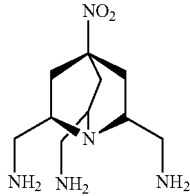

(IVb)

with a compound of formula (V)

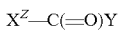 (V)

wherein $X^Z$ is X as defined earlier and wherein the hydroxyl groups which are bound to X are protected; and Y is a leaving group;

b) reducing the nitro group to obtain an amino group;

c) reacting the product obtained with a compound of formula $(IX_{A*})$

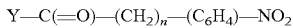 $(IX_{A*})$ wherein Y and n are as defined above;

d) reducing the nitro group to an amino group;

e) reacting the amino group with thiophosgene to give the isothiocyanate group —N=C=S; and f) removing the hydroxyl protecting groups of $X^Z$.

Compounds of formula (I) wherein $R^1$ is $NH_2$ are readily obtained from compounds of formula (VIa) and (VIb) by reducing the nitro group present in these compounds by hydrogenation with a Rayney nickel catalyst in a solvent such as methanol. If compounds of formula (I) wherein $R^1$ is $NH_2$ are the desired end product, the protecting groups for hydroxyl groups in the chelator moiety X are removed by for instance hydrogenation with a palladium catalyst or acid cleavage of benzyl protection groups. It is also possible to reduce the nitro group and remove the protecting groups for hydroxyl groups simultaneously, e.g. by using a catalyst mixture of Rayney nickel and palladium.

If compounds of formula (I) wherein $R^1$ is $NH_2$ are used as starting compounds for the synthesis of compounds of formula (I) wherein $R^1$ is NHC(=O)$R^2$, wherein $R^2$ is $C_1$-$C_6$-alkyl, $C_6$-$C_{15}$-aryl, $C_7$-$C_{22}$-arylakl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$ wherein n is 0 to 6 and m is 1 to 6, the hydroxyl protecting groups in the chelator moiety X may or may not be present. If $R^2$ is $(CH_2)_n$—$(C_6H_4)$—NCS the hydroxyl protecting groups should not be present as the deprotection (hydrogenation) is poisoned by the presence of an isothiocyanate group —NCS. For all other cases, it is preferred that the hydroxyl protecting groups are present since it was observed that their presence gives better yields.

The reactions discussed above are illustrated in reaction scheme 5:

Reaction scheme 5.

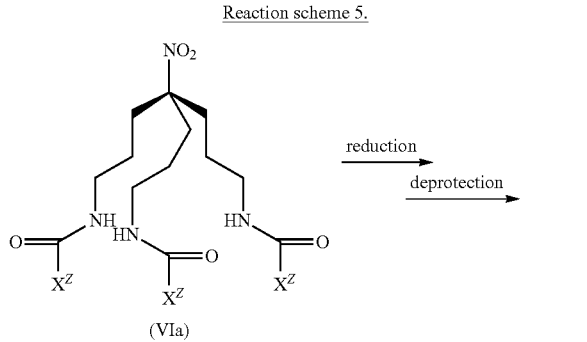

(VIa)

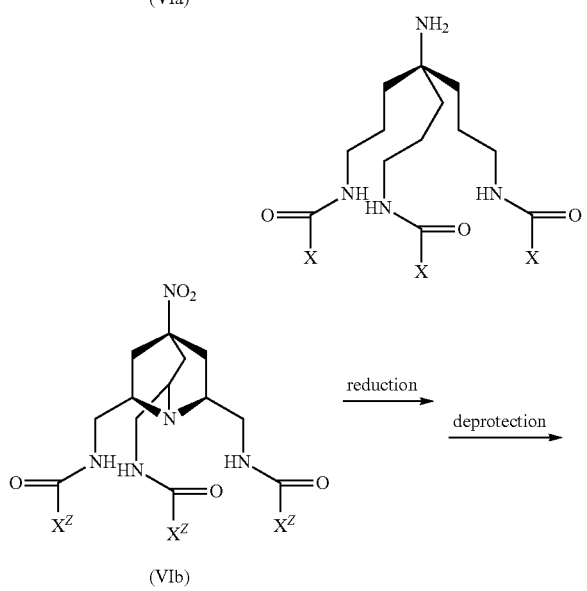

(VIb)

In the following, optionally protected compounds of formula (I) wherein $R^1$ is $NH_2$ are denoted compounds of formula (VIIIa) and (VIIIb)

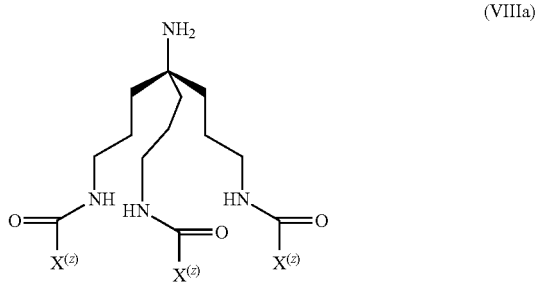

(VIIIa)

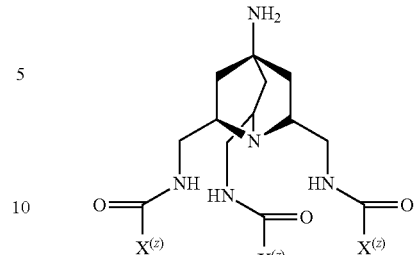

(VIIIb)

and $X^{(Z)}$ indicates that the hydroxyl protecting group Z may or may not be present in the chelator X of said compounds.

Compounds of formula (VIIIa) or (VIIIb) are readily reacted with compounds of formula (IX)

$$Y\text{—}C(\text{=}O)R^2 \quad \quad \quad (IX)$$

wherein Y is defined as above and $R^2$ is $C_1$-$C_6$-alkyl, $C_6$-$C_{15}$-aryl, $C_7$-$C_{22}$-arylalkyl, O—$C_1$-$C_6$-alkyl or O—$C_7$-$C_{22}$-arylalkyl to obtain compounds of formula (I) wherein $R^1$ is NHC(=O)$R^2$, wherein $R^2$ is $C_1$-$C_6$-alkyl, $C_6$-$C_{15}$-aryl, $C_7$-$C_{22}$-arylalkyl, O—$C_1$-$C_6$-alkyl or O—$C_7$-$C_{22}$-arylalkyl.

Such compounds of formula (I) are the preferred embodiment if compounds of formula (I) are not linked to other molecules. Compounds of formula (IX) wherein $R^2$ is $C_1$-$C_6$-alkyl, $C_6$-$C_{15}$-aryl, $C_7$-$C_{22}$-arylalkyl, O—$C_1$-$C_6$-alkyl or O—$C_7$-$C_{22}$-arylalkyl are commercially available compounds or available via synthetic routes which are well known in the art.

To produce compounds of formula (II), compounds of formula (I) obtained by the synthetic routes discussed above are reacted with a chosen paramagnetic metal ion M, preferably in the form of its salt, e.g. nitrate, chloride, acetate and sulphate salts, in water as a solvent. Alternatively, an oxide of said chosen paramagnetic metal ion M may be used, e.g. $Gd_2O_3$, and a solution of the compound of formula (I) is then stirred with said oxide. This method is often preferred since it avoids the problem of free residual paramagnetic metal ions being present in the reaction product.

Thus in another aspect the invention provides a method for producing a compound of formula (II) by reacting a compound of formula (I) with a paramagnetic metal ion, preferably in the form of its salt or in the form of its oxide.

Compounds of formula (I) linked to other molecules via the $R^1$-group can be prepared by methods known in the art. If for instance said other molecule is a peptide, polypeptide or protein, compounds of formula (I) can be readily linked to suitable functional groups in said other molecules. By way of example, compounds of formula (I) wherein $R_1$ is $NH_2$ may be reacted with carboxyl groups in said other molecule. It may be necessary to activate the functional groups in said other molecules, e.g. generating an acyl chloride from a carboxyl group. Methods to activate functional groups in order to enhance their reactivity are known to the skilled person in the art (see for example Sandler and Karo, eds. Organic Functional Group preparation, Academic Press, San Diego 1998).

Compounds of formula (II) linked to other molecules via the $R^1$-group can be prepared by linking a compound of formula (I) to another molecule via the $R^1$-group as described in the previous paragraph and then reacting the product obtained with a chosen paramagnetic metal ion M to result in a compound of formula (II) linked to said another molecule. In another embodiment a compound of formula (II) is directly linked to another molecule via the $R^1$-group as described in the previous paragraph.

As previously discussed, if compounds of formula (I) are linked to large molecules like proteins, polymers or dendrimers, click chemistry is preferred to achieve said linking. Thus, in a preferred embodiment, $R^1$ is NHC(=O)$R^2$ and $R^2$ is as follows and * denotes the attachment point of $R^2$ to the carbon atom of group C(=O)$R^2$:

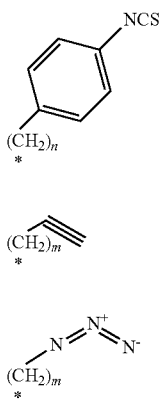

Compounds of formula (I) wherein $R^1$ is NHC(=O)$R^2$ and $R^2$ is (B) or (C), i.e. (CH$_2$)$_m$—C≡CH or (CH$_2$)$_m$—N$_3$ can be prepared by reacting a compound of formula (IX)

Y—C(=O)$R^2$   (IX)

wherein $R^2$ is (B) or (C) as defined above and Y is a leaving group as defined above with compounds of formula (VIIIa) or (VIIIb) to result compounds of formula (Xa) and (Xb). This reaction is illustrated in reaction scheme 6:

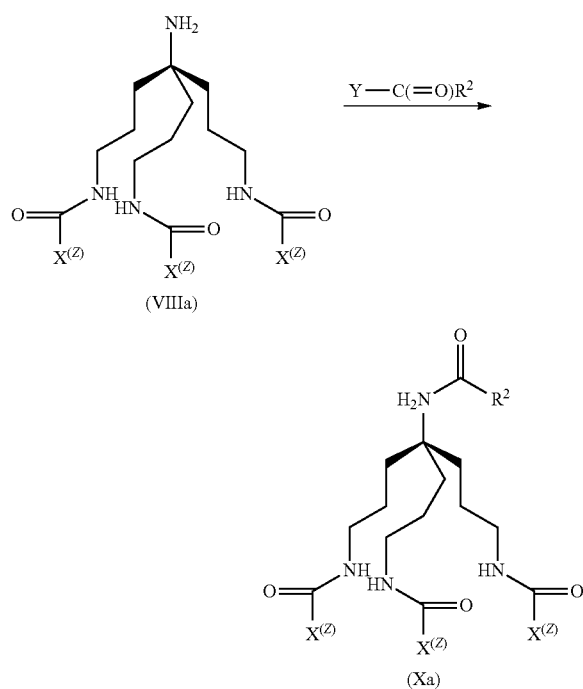

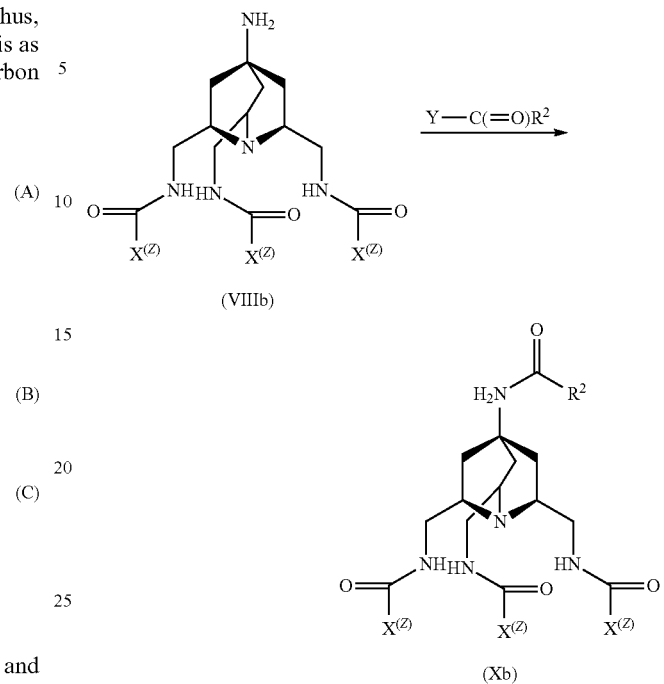

Compounds of formula (I) wherein $R^1$ is NHC(=O)$R^2$ and $R^2$ is (A), i.e. (CH$_2$)$_n$—(C$_4$H$_6$)—NCS can be prepared by a) reacting a compound of formula (IX$_{A*}$)

Y—C(=O)—(CH$_2$)$_n$—(C$_6$H$_4$)—NO$_2$   (IX$_{A*}$)

wherein n is defined as above and Y is a leaving group as defined above with compounds of formula (VIIIa) or (VIIIb);

b) reducing the nitro group to an amino group; and c) reacting the amino group with thiophosgene to give the isothiocyanate group —N=C=S.

Compounds of formula (IX$_{A*}$) may be prepared by for instance reacting a carboxylic acid of formula HOOC—(CH$_2$)$_n$—(C$_4$H$_6$)—NO$_2$ and N-hydroxysuccinimide in the presence of a coupling agent such as dicyclohexylcarbodiimide (DCC).

Compounds of formula (IX) wherein $R^2$ is (B) may be prepared by for instance reacting an ω-alkynoic acid HOOC—(CH$_2$)$_m$—C≡CH with N-hydroxysuccinimide in the presence of a coupling agent such as DCC.

Compounds of formula (IX) wherein $R^2$ is (C) may be prepared by for instance reacting an ω-azido carboxylic acid HOOC—(CH$_2$)$_m$—N$_3$ with N-hydroxysuccinimide in the presence of a coupling agent such as DCC.

In a subsequent step, compounds of formula (Xa) and (Xb) can be linked to another molecule, preferably a large molecule like a protein, polymer or dendrimer.

Compounds of formula (Xa) or (Xb) wherein $R^2$ is (A) are readily linked to other (large) molecules comprising amino groups. This reaction is shown in reaction scheme 7A:

Reaction scheme 7A.

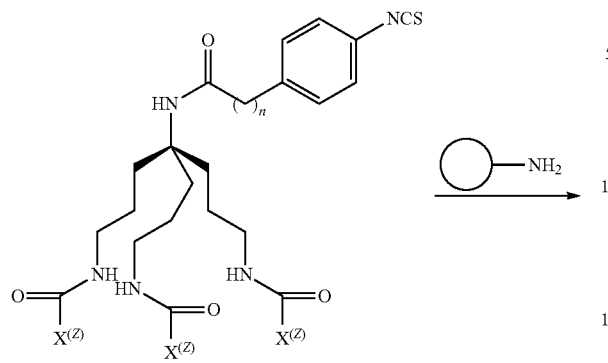

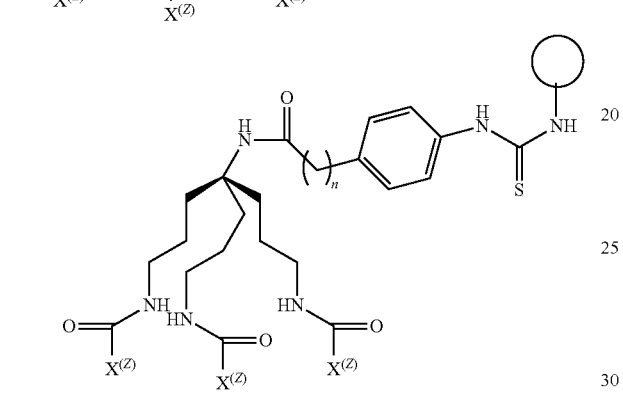

Reaction scheme 7B.

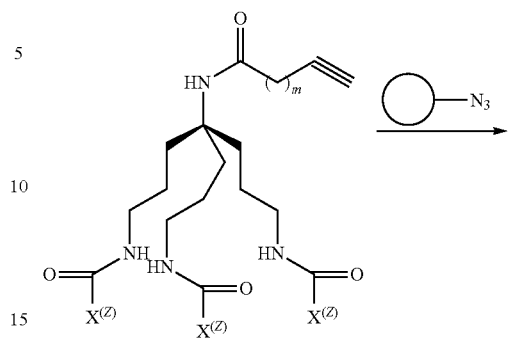

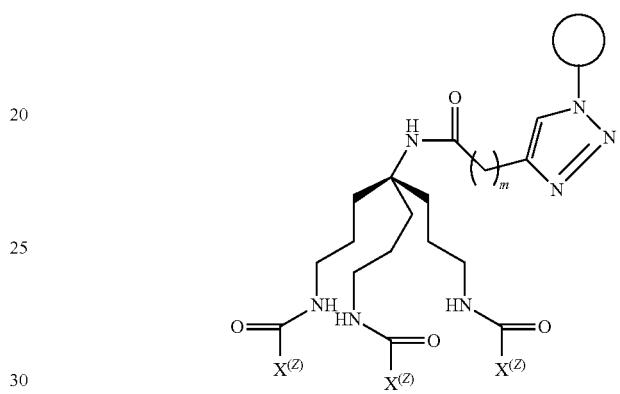

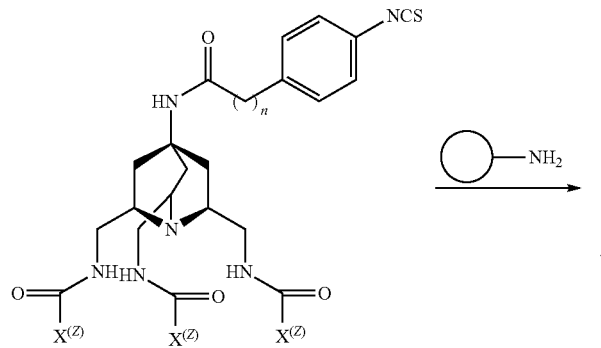

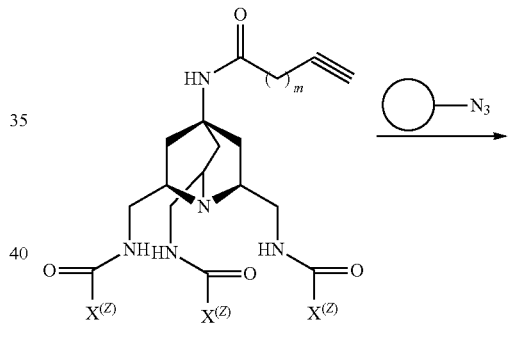

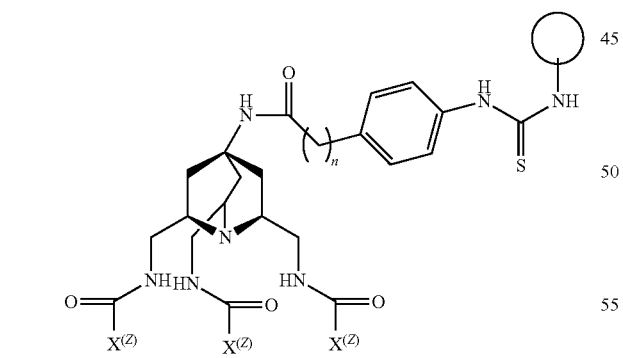

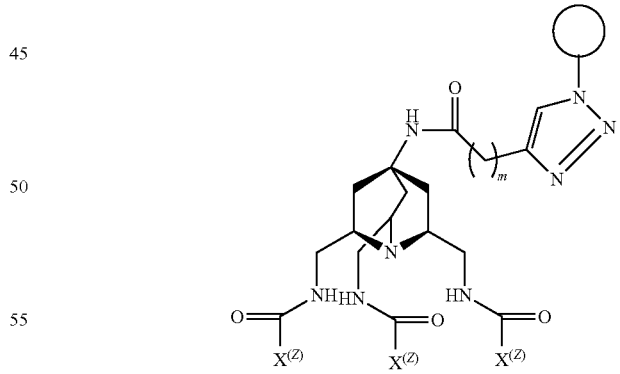

Compounds of formula (Xa) or (Xb) wherein $R^2$ is (B) are readily linked to other (large) molecules comprising amino groups. This reaction is shown in reaction scheme 7B. In a preferred embodiment, this reaction is catalysed by a copper catalyst prepared by for instance, reacting copper sulphate with ascorbic acid.

Compounds of formula (Xa) or (Xb) wherein $R^2$ is (C) are readily linked to other (large) molecules comprising amino groups. This reaction is shown in reaction scheme 7C. In a preferred embodiment, this reaction is catalysed by a copper catalyst prepared by for instance, reacting copper sulphate with ascorbic acid.

Reaction scheme 7C.

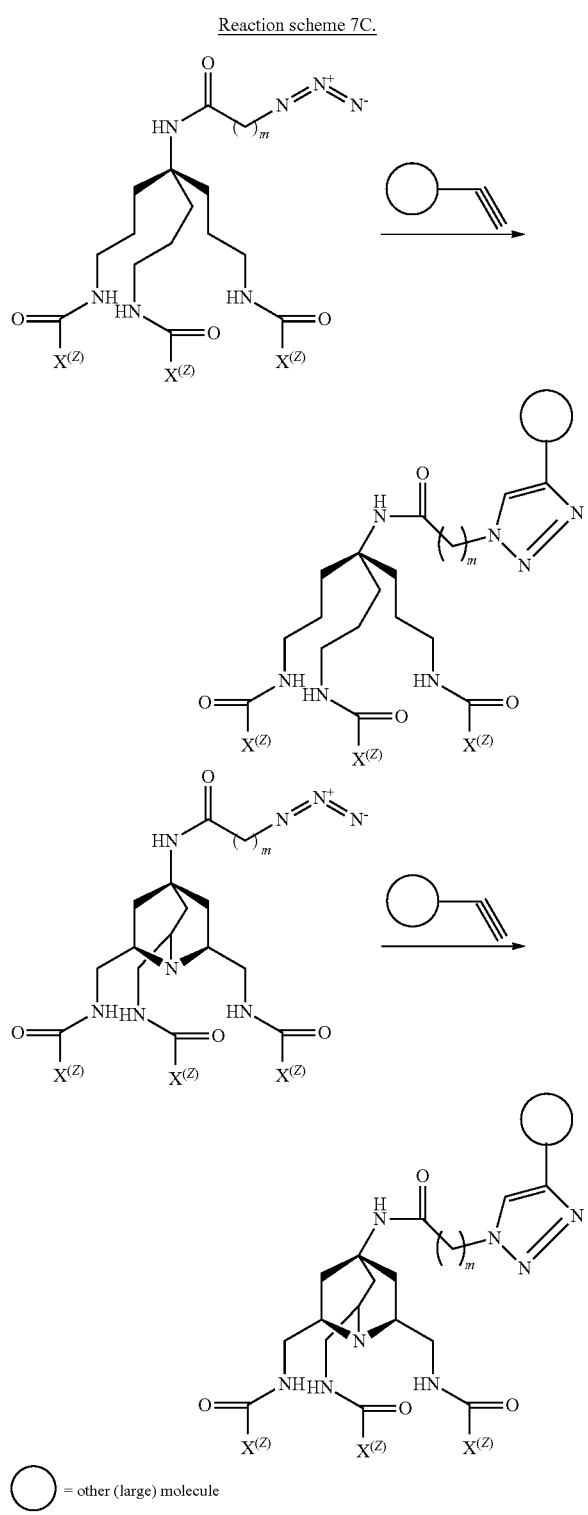

◯ = other (large) molecule

Compounds of formula (II) and compounds of formula (II) linked to other molecules, preferably to natural or synthetic peptides, peptidomimetics, polypeptides, proteins, antibodies, natural or synthetic polymers, dendrimers, lipophilic compounds or nanoparticles may be used as MR contrast agents.

For this purpose, the compounds of formula (II) and compounds of formula (II) linked to other molecules are formulated with conventional physiologically tolerable carriers like aqueous carriers, e.g. water and buffer solutions, and optionally with excipients. The resulting composition is denoted "MR contrast medium".

Thus in a further aspect the invention provides a composition comprising a compound of formula (II) or a compound of formula (II) linked to other molecules and at least one physiologically tolerable carrier. Said composition may be used as MR contrast medium in MRI.

To be used as MR contrast medium in MRI of the human and non-human animal body, said MR contrast medium needs to be suitable for administration to said body. Suitably, the compounds of formula (II) or compounds of formula (II) linked to other molecules and optionally pharmaceutically acceptable excipients and additives may be suspended or dissolved in at least one physiologically tolerable carrier, e.g. water or buffer solution(s). Suitable additives include for example physiologically compatible buffers like tromethamine hydrochloride, chelators such as DTPA, DTPA-BMA or compounds of formula (I), weak complexes of physiologically tolerable ions such as calcium chelates, e.g. calcium DTPA, CaNaDTPA-BMA, compounds of formula (I) wherein X forms a complex with $Ca^{2+}$ or Ca/Na salts of compounds of formula (I), calcium or sodium salts like calcium chloride, calcium ascorbate, calcium gluconate or calcium lactate. Excipients and additives are further described in e.g. WO-A-90/03804, EP-A-463644, EP-A-258616 and U.S. Pat. No. 5,876,695, the content of which are incorporated herein by reference.

Another aspect of the invention is the use of a composition comprising a compound of formula (II) or a compound of formula (II) linked to another molecule and at least one physiologically tolerable carrier as MR imaging medium.

Yet another aspect of the invention is a method of MR imaging wherein a composition comprising a compound of formula (II) or a compound of formula (II) linked to another molecule and at least one physiologically tolerable carrier is administered to a subject and the subject is subjected to an MR examination wherein MR signals are detected from the subject or parts of the subject into which the composition distributes and optionally MR images and/or MR spectra are generated from the detected signals. In a preferred embodiment, the subject is a living human or non-human animal body.

In a further preferred embodiment, the composition is administered in an amount which is contrast-enhancing effective, i.e. an amount which is suitable to enhance the contrast in the method of MR imaging.

In another preferred embodiment, the subject is a living human or non-human animal being and the method of MR imaging is a method of MR tumour detection or a method of tumour delineation imaging.

In another aspect, the invention provides a method of MR imaging wherein a subject which had been previously administered with a composition comprising a compound of formula (II) or a compound of formula (II) linked to another molecule and at least one physiologically tolerable carrier is subjected to an MR examination wherein MR signals are detected from the subject or parts of the subject into which the composition distributes and optionally MR images and/or MR spectra are generated from the detected signals.

The term "previously been administered" means that any step requiring a medically-qualified person to administer the composition to the patient has already been carried out before the method of MR imaging and/or MR spectroscopy according to the invention is commenced.

The invention will now be described in greater detail by way of the following non-limiting examples.

EXAMPLES

Example 1

1a) Tris[2-(carboxyaminoprop-3-yl)-3-oxy-1-(2-methoxyethyl)-4-oxo-1,4-dihydro-pyridine]nitromethane Gadolinium (III)

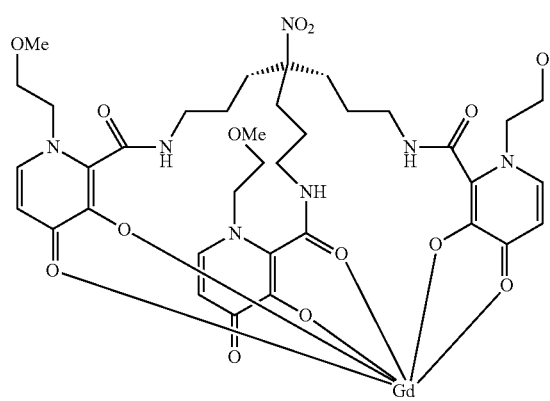

1b) Tris[2-(carboxyaminoprop-3-yl)-3-oxy-1-(2-methoxyethyl)-4-oxo-1,4-dihydro-pyridine]nitromethane Lanthanum (III)

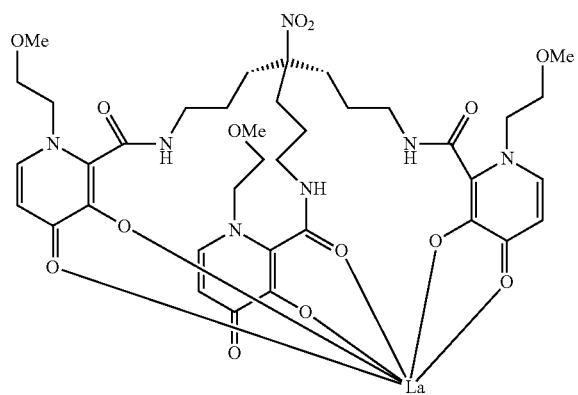

1c) 4-Nitro-1,7-bis{N-tert-butoxycarbonylamino}-4-{3-N-[tert-butoxy-carbonyl amino]propyl}heptane

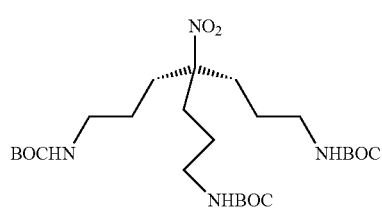

The compound was prepared in two steps from tris-(2-cyanoethyl)nitromethane in 70% yield according to S. Lebreton et al., Tetrahedron 59 (2003), 3945-3953.

$^1$H-NMR (300 MHz, CDCl$_3$): δ 4.71 (3H, bs, NH); 3.09 (6H, m, 3×CH$_2$—NH); 1.88 (6H, m, 3×CH$_2$—C—NO2); 1.45 (33H, m, 9×CH$_3$+3×CH$_2$)

$^{13}$C NMR (300 MHz, CDCl$_3$): δ 155.97, 93.77, 79.32, 40.12, 32.54, 28.33, 24.20.

1d) 1,7-diamino-4-nitro-4-(3-amino-propyl)-heptane Trifluoroacetic acid salt

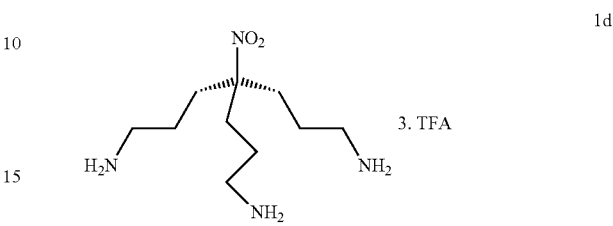

Trifluoroacetic acid (15 ml) was added to a solution of 1c (2.1 g, 4 mmol) in dry DCM (15 ml). The mixture was stirred at room temperature for 5 h. The solvents were removed in vacuo and the residue was freeze-dried to give the title compound 1d as trifluoroacetic acid adduct (colourless oil, 2.3 g, 100%).

$^1$H-NMR (300 MHz, CD$_3$OD): δ 2.97 (6H, m, 3×CH$_2$—NH); 2.07 (6H, m, 3×CH$_2$—C—NO2); 1.66 (6H, m, 3×CH$_2$)

$^{13}$C NMR (75.5 MHz, CD$_3$OD): δ 162.24, 161.73, 161.24, 160.75, 94.16, 40.31, 33.17, 22.91.

1e) Tris[2-(carboxyaminoprop-3-yl)-3-benzyloxy-4-oxo-4H-pyran]nitromethane

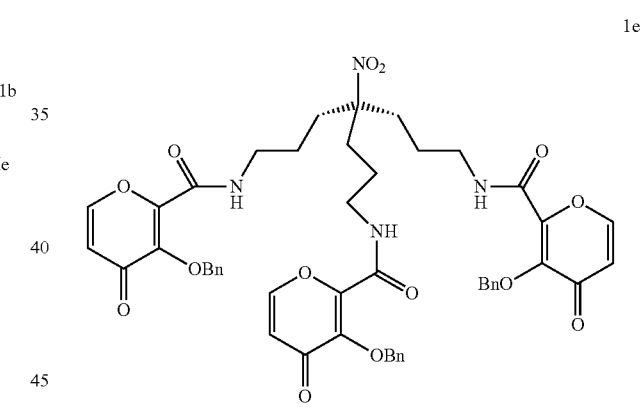

A solution of 3-benzyloxy-4-oxo-4H-pyran-2-carboxylic acid 2,5-dioxo-pyrrolidin-1-yl ester prepared as described in J. Amer. Chem. Soc. 2006, 2222-2223 (1.6 g, 4.7 mmol) in anhydrous THF (10 ml) was added to a mixture of 1d (0.86 g, 1.5 mmol) and triethylamine (1.3 ml, 9.2 mmol) in anhydrous THF (20 ml) and stirred at room temperature for 24 h. The reaction mixture was concentrated under reduced pressure, the residue partitioned between water and dichloromethane and the organic layer dried (Na$_2$SO$_4$), and concentrated under reduced pressure. The residue was purified by column chromatography on silica, eluting with 3-5% MeOH/CH$_2$Cl$_2$ to give the title compound 1e as a pale yellow solid (0.57 g, 42%).

$^1$H-NMR (300 MHz, CDCl$_3$): δ 7.81 (3H, d, J=5.9 Hz, CH); 7.74 (3H, bt, NH); 7.36 (15H, s, ArH); 6.47 (3H, d, J=5.9 Hz, CH); 5.39 (6H, s, 3×ArCH$_2$); 3.14 (6H, m, 3×CH$_2$—NH); 1.67 (6H, m, 3×CH$_2$—C—NO2); 1.14 (6H, m, 3×CH$_2$).

$^{13}$C NMR (300 MHz, CDCl$_3$): δ 177.01, 160.38, 155.92, 148.59, 148.05, 136.67, 130.74, 130.48, 130.33, 118.93, 94.41, 77.93, 40.60, 33.85, 24.70.

m/z (ES+) 917 (M+H).

1f) Tris[2-(carboxyaminoprop-3-yl)-3-benzyloxy-1-(2-methoxyethyl)-4-oxo-1,4-dihydro-pyridine]nitromethane

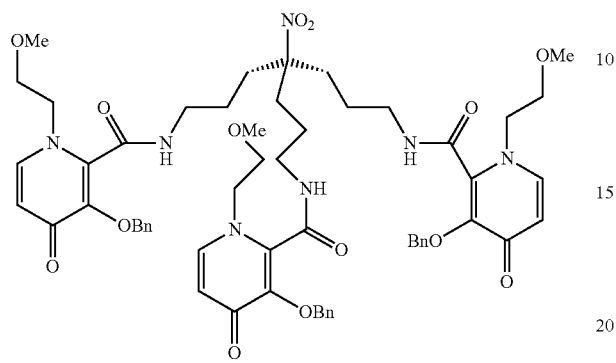

1f

To a solution of 1e (0.55 g, 0.6 mmol) in methanol (15 ml) was added 2-methoxyethylamine (0.41 ml, 4.8 mmol) and the reaction heated to reflux for 1 h. The reaction mixture was concentrated under reduced pressure and the residue was purified by column chromatography on silica, eluting with 20-50% MeOH/CH$_2$Cl$_2$ to give the title compound 1f as a yellow solid (370 mg, 57%).

$^1$H-NMR (300 MHz, CDCl$_3$): δ 8.09 (3H, bt, NH); 7.27 (18H, m, ArH+3×CH); 6.08 (3H, d, J=7.4 Hz, CH); 4.93 (6H, s, 3×ArCH$_2$); 3.90 (6H, m, 3×CH$_2$—N); 3.62 (6H, m, 3×CH$_2$—O); 3.27 (9H, s, OMe); 3.05 (6H, m, 3×CH$_2$—NH); 1.57 (6H, m, 3×CH$_2$—C—NO2); 1.14 (6H, m, 3×CH$_2$).

$^{13}$C NMR (300 MHz, CDCl$_3$): δ 176.47, 163.71, 147.57, 142.77, 142.36, 139.71, 131.06, 131.01, 120.19, 95.52, 79.31, 73.79, 61.59, 56.98, 41.72, 35.16, 25.82 m/z (ES+) 1088 (M+H).

1g) Tris[2-(carboxyaminoprop-3-yl)-3-hydroxy-1-(2-methoxyethyl)-4'-oxo-1,4-dihydro-pyridine]nitromethane

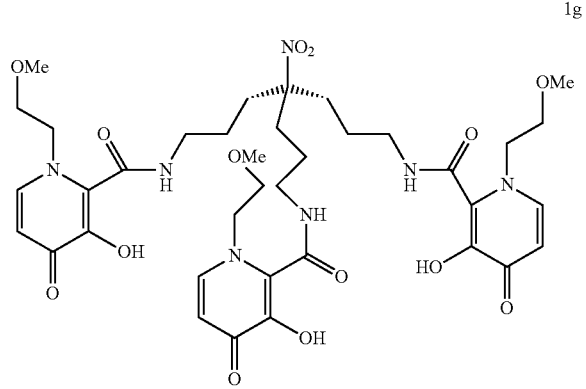

1g

Compound 1f (422 mg, 0.4 mmol) was stirred in glacial acetic acid (6 ml) and conc. HCl (6 ml) and heated at 35° C. for 3 days. The reaction mixture was concentrated under reduced pressure to give the title compound 1g as light brown crystals (300 mg, 94%).

$^1$H-NMR (300 MHz, CD$_3$OD): δ 8.16 (3H, d, J=6.8 Hz, CH); 7.17 (3H, d, J=6.8 Hz, CH); 4.51 (6H, m, 3×CH$_2$—N); 3.76 (6H, m, 3×CH$_2$—O); 3.48 (6H, m, 3×CH$_2$—NH); 3.30 (9H, s, OMe); 2.12 (6H, m, 3×CH$_2$—C—NO2); 1.64 (6H, m, 3×CH$_2$).

$^{13}$C NMR (300 MHz, CD$_3$OD): δ 163.49, 161.18, 145.21, 141.27, 137.32, 112.61, 95.27, 71.57, 59.28, 58.13, 40.75, 34.23, 24.52 m/z (ES+) 818 (M+H).

1a) Tris[2-(carboxyaminoprop-3-yl)-3-oxy-1-(2-methoxyethyl)-4-oxo-1,4-dihydro-pyridine]nitromethane Gadolinium (III)

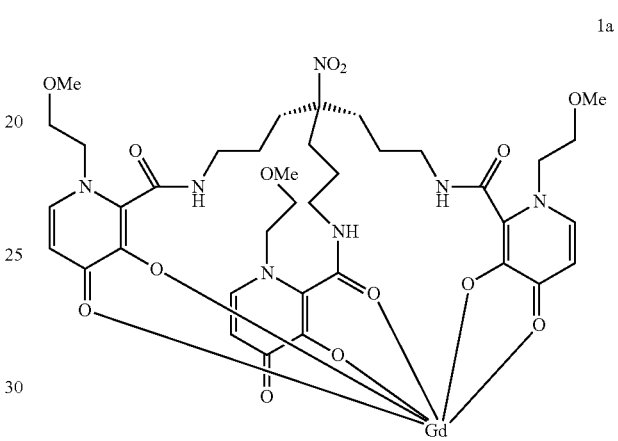

1a

To a solution of 1g (50 mg, 0.06 mmol) in methanol (1 ml) and water (1 ml) was added gadolinium(III)nitrate hexahydrate (27 mg, 0.06 mmol) and pyridine (0.15 ml). The reaction was stirred at room temperature for 24 hrs, filtered, washed with methanol (7×5 ml) to give the title compound 1a as a pale brown solid (31 mg, 53%).

1b) Tris[2-(carboxyaminoprop-3-yl)-3-oxy-1-(2-methoxyethyl)-4-oxo-1,4-dihydro-pyridine]nitromethane Lanthanum (III)

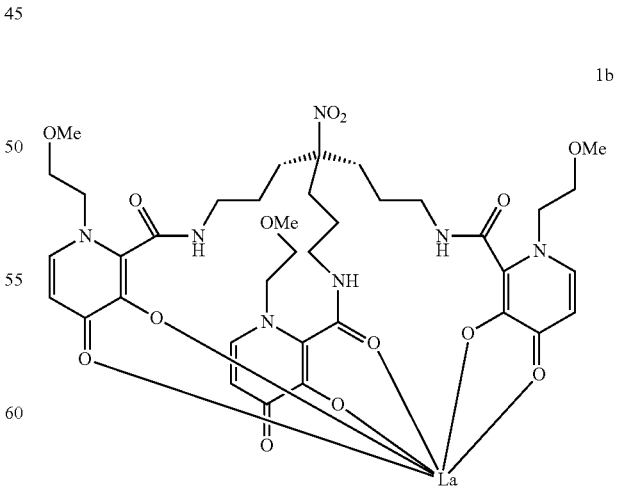

1b

To a solution of 1g (50 mg, 0.06 mmol) in methanol (1 ml) and water (1 ml) was added lanthanum(III)nitrate hexahydrate (26 mg, 0.06 mmol) and pyridine (0.15 ml). The reaction was stirred at room temperature for 2 hrs, filtered, washed with methanol (7×5 ml) to give the title compound 1b as a pale pink solid (48 mg, 84%).

$^1$H-NMR (300 MHz, DMSO-$d_6$): δ 10.5 (3H, bs, NH); 7.54 (3H, d, J=6.7 Hz, CH); 6.16 (3H, d, J=6.7 Hz, CH); 4.55 (6H, bs, 3×CH$_2$—N); 3.5 (6H, s, 3×CH$_2$—O); 3.27 (6H, bs, 3×CH$_2$—NH); 3.17 (9H, s, OMe); 1.94 (6H, bs, 3×CH$_2$—C—NO2); 1.38 (6H, bs, 3×CH$_2$).

Example 2

2) Gadolinium (III) complex of tris((3-hydroxy-4-oxo-4H-pyran-2-yl)carbonylamino-propyl))nitromethane

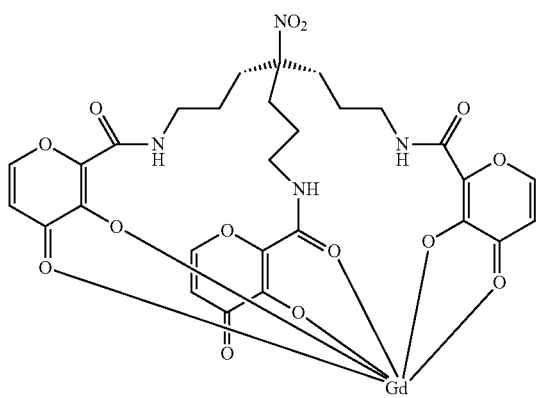

2a) Tris((3-hydroxy-4-oxo-4H-pyran-2-yl)carbonylaminoprop-3-yl)nitromethane

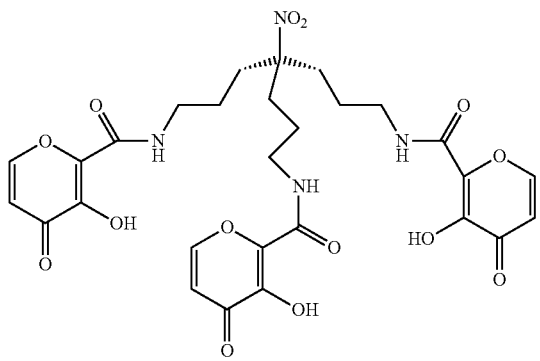

A mixture of 1e (0.10 g, 0.11 mmol), glacial acetic acid (1 ml) and concentrated hydrochloric acid (1 ml) was stirred at room temperature for 18 h. The reaction mixture was concentrated in vacuo, the residue azeotroped several times with methanol (10 ml) to afford the title compound 2a (64 mg, 90%) as a yellow solid.

$^1$H NMR (300 MHz, DMSO) δ 1.41 (m, 6H), 1.89 (m, 6H), 3.27 (m, 6H), 6.44 (d, 5.6 Hz, 3H), 8.13 (d, J=5.5 Hz, 3H), 8.88 (bt, 3H, NH), 11.4 (bs, 3H).

2) Gadolinium (III) complex of tris((3-hydroxy-4-oxo-4H-pyran-2-yl)carbonylamino-propyl))nitromethane

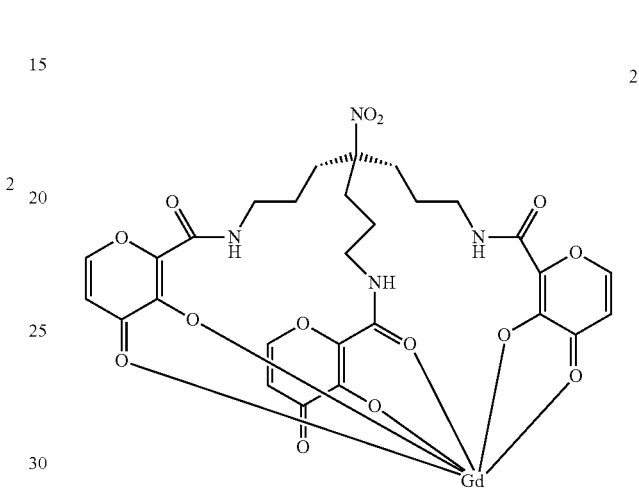

2a (0.1 g, 0.15 mmol) was dissolved in a mixture of hot methanol (60 ml) and water (30 ml). Gadolinium (III)nitrate hexahydrate (63 mg, 0.14 mmol) and pyridine (0.42 ml) was added to the hot solution. The reaction mixture was heated to reflux for 2 h, concentrated in vacuo, filtered and washed with methanol (7×5 ml) to afford the title compound 2 (108 mg, 90%) as a pale orange solid.

Example 3

3) Tris((3-hydroxy-1-(2-hydroxyethyl)-4-oxo-4H-pyridin-2-yl)carbonylamino-propyl)aminomethane

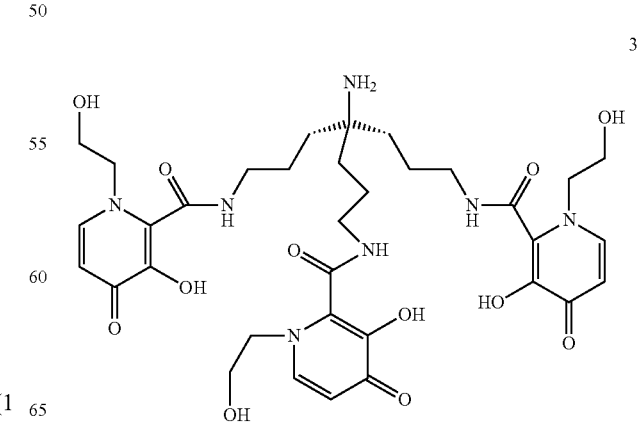

3a) Tris((3-benzyloxy-1-(2-hydroxyethyl)-4-oxo-4H-pyridin-2-yl)carbonyl-aminopropyl)nitromethane

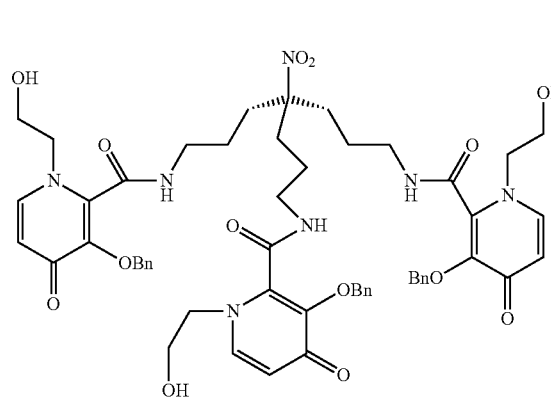

3a

A mixture of 1e (0.50 g, 0.55 mmol), 2-ethanolamine (0.27 g, 4.4 mmol) in anhydrous methanol (10 ml) under nitrogen was heated to reflux for 1 h. The reaction mixture was concentrated in vacuo and the residue purified by column chromatography on silica, eluting with 30-70% MeOH/DCM to afford the title compound 3a (260 mg, 45%) as a yellow solid. The sample was azeotroped with Methanol/toluene 1:1 to remove final traces of 2-ethanolamine.

$^1$H NMR (300 MHz, CD$_3$OD) δ 1.19 (m, 6H), 1.66 (m, 6H), 3.14 (m, 6H), 3.83 (m, 6H), 4.00 (m, 6H), 5.06 (s, 6H), 6.45 (d, J=7.7 Hz, 3H), 7.35 (m, 15H), 7.71 (d, J=7.7 Hz, 3H).
$^{13}$C NMR (75 MHz, CD$_3$OD) δ 24.4, 33.8, 40.5, 57.9, 61.9, 75.6, 94.7, 118.5, 129.4, 129.6, 129.7, 138.3, 142.0, 142.2, 146.3, 162.8, 175.7
m/z (ES$^-$) 1044.4 (M$^-$H)$^-$.

3b) Tris((3-benzyloxy-1-(2-hydroxyethyl)-4-oxo-4H-pyridin-2-yl)carbonylaminopropyl)aminomethane

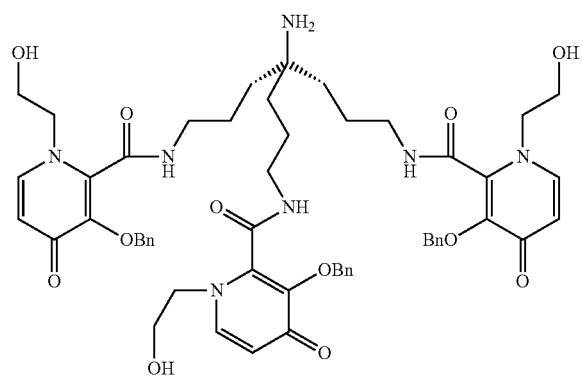

3b

A mixture of 3a (AH113249) (0.11 g, 0.11 mmol) and Raney nickel (1.4 g) in ethanol (20 ml) was hydrogenated at 2 bar at 40° C. for 24 h. The reaction mixture was filtered through glass fibre filter paper and solvents removed in vacuo to afford the title compound 3b (70 mg, 63%) as an orange solid.

$^1$H NMR (300 MHz, CD$_3$OD) δ 1.17 (m, 6H), 1.28 (m, 6H), 3.20 (m, 6H), 3.83 (m, 6H), 4.03 (m, 6H), 5.10 (s, 6H), 6.50 (bs, 3H), 7.20-7.50 (m, 15H), 7.74 (bs, 3H).
$^{13}$C NMR (75 MHz, CD$_3$OD) δ 24.0, 37.5, 41.3, 54.2, 57.9, 61.9, 75.4, 118.5, 129.3, 129.5, 138.6, 142.1, 142.2, 146.6, 162.8, 176.0, 180.2
m/z (ES$^+$) 1016.5 (M$^+$H)$^+$.

3) Tris((3-hydroxy-1-(2-hydroxyethyl)-4-oxo-4H-pyridin-2-yl)carbonylamino-propyl)aminomethane

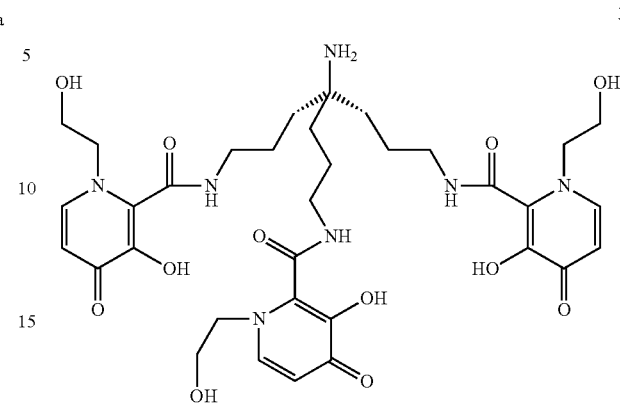

3

To a solution of 3b (70 mg, 0.07 mmol) in methanol (15 ml) was added palladium 10% wt on activated carbon (100 mg). The mixture was hydrogenated at 2 bar at room temperature for 24 h. The reaction mixture was filtered twice through glass fibre filter paper and solvents removed in vacuo to afford the title compound 3 (43 mg, 82%) as an orange solid.

$^1$H NMR (300 MHz, D$_2$O) δ 1.50-2.00 (m, 12H), 3.40 (m, 6H), 3.76 (m, 6H), 4.20 (m, 6H), 6.34 (bs, 3H), 7.43 (bs, 3H).

Example 4

4) N-Tris(3-hydroxy-1-(2-hydroxyethyl)-4-oxo-4H-pyridin-2-yl)carbonylamino-propyl)methyl benzamide

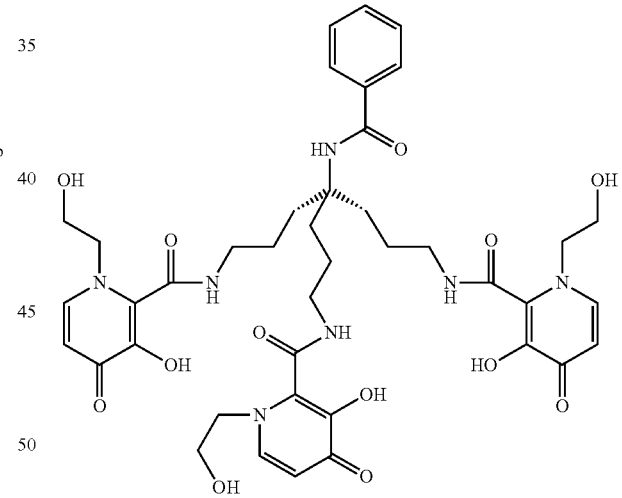

4

4a) Tris(3-tert-butoxycarbonylaminopropyl)aminomethane

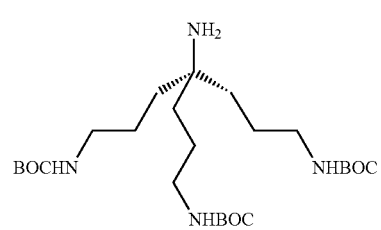

4a

Tris(3-(tertbutoxycarbonylamino)propyl)nitromethane 1c (30 g, 59.8 mmol) and Raney nickel (30 g) in ethanol (300 ml)

was hydrogenated at 30 psi at room temperature for 18 h. The reaction was cautiously filtered through a glass fibre filter paper avoiding sucking the catalyst dry to avoid ignition. The solution was concentrated in vacuo to afford the title compound 4a (27.2 g, 87%) as a white foam.

$^1$H NMR (300 MHz, CDCl$_3$) δ 1.39 (bs, 39H), 3.05 (m, 6H), 4.73 (bs, 3H).

$^{13}$C NMR (75 MHz, CDCl$_3$) δ 24.1, 28.3, 37.0, 40.9, 52.7, 79.4, 155.9.

4b) N-(Tris(3-tert-butoxycarbonylaminopropyl)methyl)benzamide

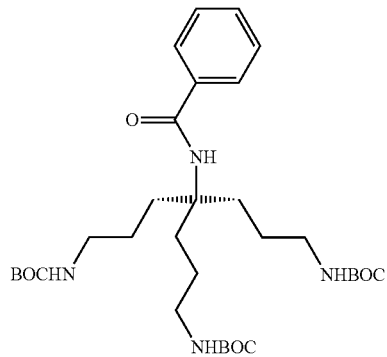

A stirred solution of 4a (AH113156) (5.5 g, 11.0 mmol) in dichloromethane (100 ml) was treated with triethylamine (1.25 g, 12.4 mmol) and benzoyl chloride (1.73 g, 12.4 mmol) at room temperature for 2 h. The reaction was then treated with water (5 ml) and stirred for a further 0.5 h. The dichloromethane solution was washed with 10% aqueous potassium carbonate solution, separated, dried over sodium sulfate and concentrated in vacuo to a crisp solid (6.3 g). Chromatography on silica in a gradient of 3-10% methanol in dichloromethane gave the title compound 4b (4.34 g, 65%) as a white solid.

$^1$H NMR (300 MHz, CDCl$_3$) δ 1.37, (bs, 33H), 1.72 (m, 6H), 3.04 (m, 6H), 4.79 (m, 3H), 5.75 (s, 1H), 7.34 (m, 3H), 7.64 (d, J=7.0 Hz, 2H).

$^{13}$C NMR (75 MHz, CDCl$_3$) δ 23.8, 28.3, 32.2, 40.6, 58.6, 79.5, 126.6, 128.4, 131.2, 135.3, 156.0, 166.9

4c) N-(Tris(3-benzyloxy-4-oxo-4H-pyran-2-yl)carboxyaminopropyl)methyl benzamide

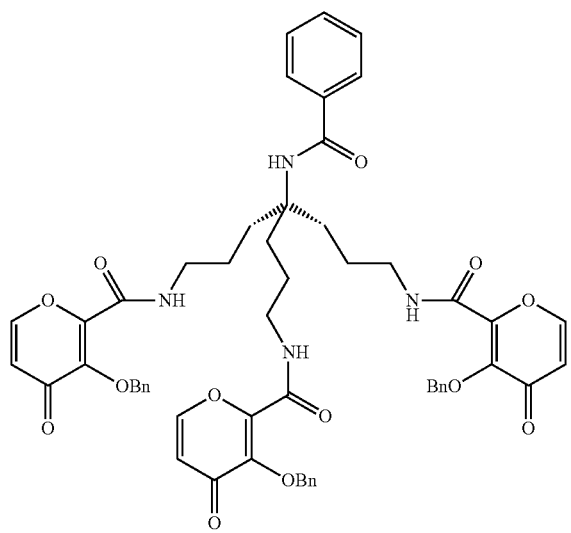

A mixture of 4b (3.52 g, 5.4 mmol) and triethylamine (3.5 g, 34.6 mmol) in dry THF (40 ml) was treated with N-hydroxysuccinimidyl-3-benzyloxy-4-oxo-4-H-pyran-2-carboxylate (S. M. Cohen, D. T. Puerta, and K. N. Raymond, J. Amer. Chem. Soc. 2006, 128, 2222). (5.80 g, 16.9 mmol) and stirred at room temperature for 24 h. Solvents were removed in vacuo, the residue partitioned between water and DCM, the aqueous layer extracted with DCM (2×30 ml), the combined organics dried over MgSO$_4$, filtered and solvents removed in vacuo to afford a gum (7 g). Chromatography on silica in a gradient of 1-10% methanol in dichloromethane gave the title compound 4c (4.6 g, 86%). as a pale yellow solid.

$^1$H NMR (300 MHz, CDCl$_3$) δ 1.26 (m, 6H). 1.60 (m, 6H), 3.14 (m, 6H), 5.35 (s, 6H), 6.43 (d, J=5.5 Hz, 3H), 7.24-7.74 (m, 24H), 7.77 (d, J=5.8 Hz, 3H).

$^{13}$C NMR (75 MHz, CDCl$_3$) δ 24.5, 33.6, 41.4, 59.9, 77.0, 119.1, 128.2, 130.2, 130.4, 130.6 130.7, 133.2, 136.6, 136.9, 148.5, 148.6, 156.1, 160.5, 168.3, 177.3

LC/MS (Gemini C18 5μ 4.60×50 mm, 1 ml/min, 5-95% acetonitrile/0.1% formic acid in water/0.1% formic acid over 10 minutes) showed the material at 5.05 min m/z (ES$^+$) 991.3 (M$^+$H)$^+$.

4d) N-Tris(-3-benzyloxy-1-(2-hydroxyethyl)-4-oxo-4H-pyridin-2-yl)carbonylaminopropyl)methyl benzamide

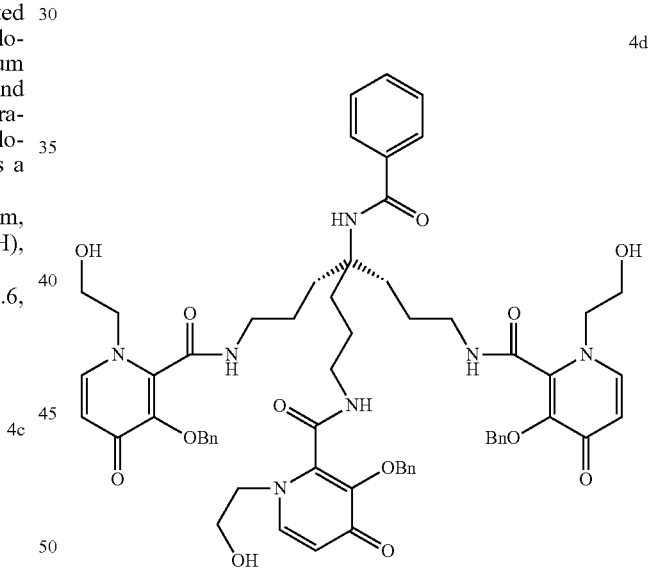

A mixture of 4c (AH113200) (0.20 g, 0.2 mmol), and 2-ethanolamine (98 mg, 1.6 mmol) in anhydrous methanol (5 ml) under nitrogen was heated to reflux for 1 h. The reaction mixture was concentrated in vacuo and the residue purified by column chromatography on silica, eluting with 10-50% MeOH/DCM to afford the title compound 4d (120 mg, 54%) as a yellow solid. The sample was azeotroped with methanol/toluene 1:1 to remove final traces of 2-ethanolamine.

$^1$H NMR (300 MHz, CD$_3$OD) δ 1.30 (m, 6H). 1.64 (m, 6H), 3.20 (m, 6H), 3.81 (m, 6H), 4.01 (m, 6H), 5.05 (s, 6H), 6.45 (d, J=7.4 Hz, 3H), 7.20-7.50 (m, 18H). 7.71 (m, 5H).

$^{13}$C NMR (75 MHz, CD$_3$OD) δ 24.0, 33.4, 41.1, 58.0, 59.8, 61.9, 75.6, 118.5, 128.3, 129.3, 129.4, 129.5, 129.6, 129.7, 132.5, 136.8, 138.3, 142.1, 142.2, 146.2, 162.7, 170.2, 175.7 m/z (ES$^+$) 1120.5 (M$^+$H)$^+$.

4) N-Tris(3-hydroxy-1-(2-hydroxyethyl)-4-oxo-4H-pyridin-2-yl)carbonylamino-propyl)methyl benzamide

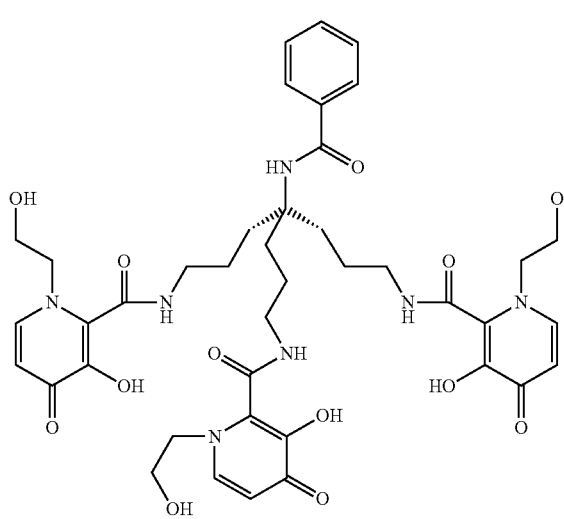

To a solution of 4c (0.10 g, 0.09 mmol) in methanol (15 ml) was added palladium 10% wt on activated carbon (0.10 g). The mixture was hydrogenated at 2 bar at room temperature for 4 h. The reaction mixture was filtered twice through glass fibre filter paper and solvents removed in vacuo to afford the title compound 4 (58 mg, 68%) as an orange solid.

$^1$H NMR (300 MHz, D$_2$O) δ 1.64 (m, 6H). 1.89 (m, 6H), 3.40 (m, 6H), 3.75 (m, 6H), 4.12 (m, 6H), 6.44 (bs, 3H), 7.20-7.90 (m, 8H).

m/z (ES$^+$) 850.3 (M$^+$H)$^+$.

Example 5

5) N-Tris(-3-hydroxy-1-(2-methoxyethyl)-4-oxo-4H-pyridin-2-yl)carbonylamino-propyl)methyl benzamide)

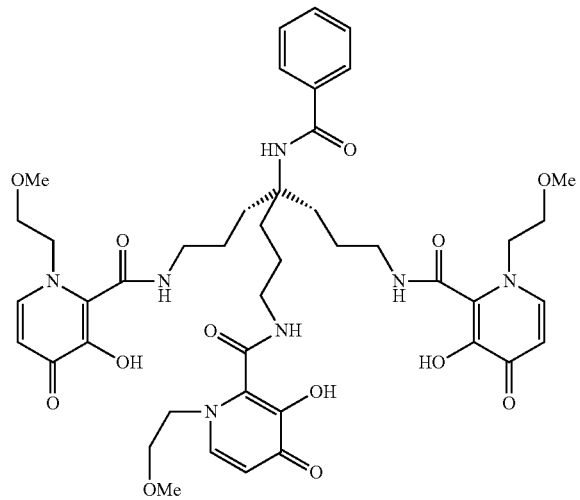

5a) N-Tris(-3-benzyloxy-1-(2-methoxyethyl)-4-oxo-4H-pyridin-2-yl)carbonylaminopropyl)methyl benzamide

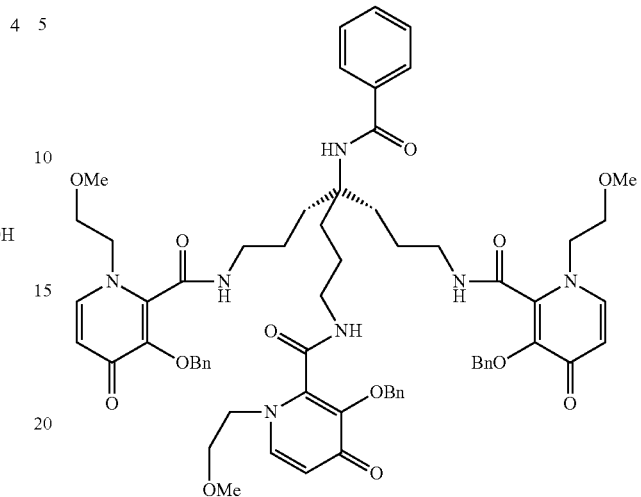

A mixture of 4c (0.30 g, 0.3 mmol), 2-methoxyethylamine (0.18 g, 2.4 mmol) in anhydrous methanol (8 ml) under nitrogen was heated to reflux for 1 h. The reaction mixture was concentrated in vacuo and the residue purified by column chromatography on silica, eluting with 10-30% MeOH/DCM to afford the title compound 5a (180 mg, 52%) as a yellow solid.

$^1$H NMR (300 MHz, CDCl$_3$) δ 1.18 (m, 6H). 1.48 (m, 6H), 3.10 (m, 6H), 3.26 (s, 9H), 3.60 (m, 6H), 3.90 (m, 6H), 4.94 (s, 6H), 6.11 (d, J=7.7 Hz, 3H), 7.10-7.80 (m, 27H).

m/z (ES$^+$) 1161.5 (M$^+$H).

5) N-Tris(-3-hydroxy-1-(2-methoxyethyl)-4-oxo-4H-pyridin-2-yl)carbonyl-aminopropyl)methyl benzamide)

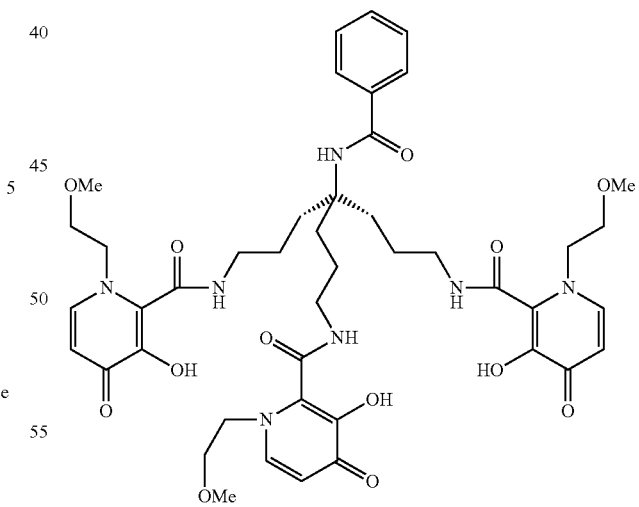

To a solution of 5a (0.10 g, 0.09 mmol) in methanol (15 ml) was added palladium 10% wt on activated carbon (0.10 g). The mixture was hydrogenated at 2 bar at room temperature for 4 h. The reaction mixture was filtered twice through glass fibre filter paper and solvents removed in vacuo to afford the title compound 5 (70 mg, 87%) as an orange solid.

$^1$H NMR (300 MHz, CD$_3$OD) δ 1.68 (m, 6H). 1.98 (m, 6H), 3.31 (s, 9H), 3.40 (m, 6H), 3.61 (m, 6H), 4.31 (m, 6H), 6.31 (bs, 3H), 7.49 (m, 5H), 7.74 (bs, 3H).

$^{13}$C NMR (75 MHz, CD$_3$OD) δ 24.3, 33.6, 41.0, 56.3, 59.2, 60.3, 72.7, 111.8, 128.4, 129.5, 132.3, 137.1, 140.7, 151.4, 164.2, 170.4, 174.0 m/z (ES$^+$) 892.4 (M$^+$H)$^+$.

Example 6

6) N-(Tris(-3-hydroxy-4-oxo-4H-pyran-2-yl)carboxyaminopropyl)methyl benzamide

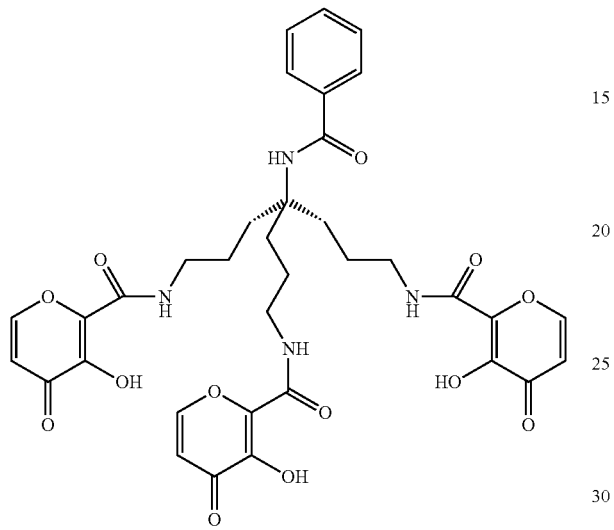

A solution of 4c (0.20 g, 0.20 mmol) in glacial acetic acid (2 ml) and concentrated hydrochloric acid (2 ml) was stirred at room temperature for 18 h. The reaction mixture was concentrated in vacuo, the residue azeotroped several times with methanol (10 ml) to afford the title compound 6 (130 mg, 90%) as a red-orange solid.

$^1$H NMR (300 MHz, DMSO) δ 1.50 (m, 6H). 1.75 (m, 6H), 3.26 (m, 6H), 6.44 (s, 3H), 0.39 (m, 4H), 7.71 (m, 2H), 8.12 (s, 3H), 8.88 (s, 3H, NH), 11.4 (bs, 3H).

$^{13}$C NMR (75 MHz, DMSO) δ 22.9, 31.5, 40.0, 58.1, 114.8, 127.3, 127.9, 130.7, 135.8, 136.9, 148.6, 154.6, 162.6, 166.5, 173.2

LC/MS (Gemini C18 5µ 4.60×50 mm, 1 ml/min, 5-95% acetonitrile/0.1% formic acid in water/0.1% formic acid over 10 minutes) showed the material at 4.40 min m/z (ES$^-$) 719.2 (M$^-$H)$^-$.

Example 7

7) Gadolinium (III) complex of Tris((3-hydroxy-1-(2,3,4,5,6-pentahydroxyhexyl)-4-oxo-4H-pyridinone-2-yl)-carboxyaminopropyl)-phenylcarboxyaminomethane

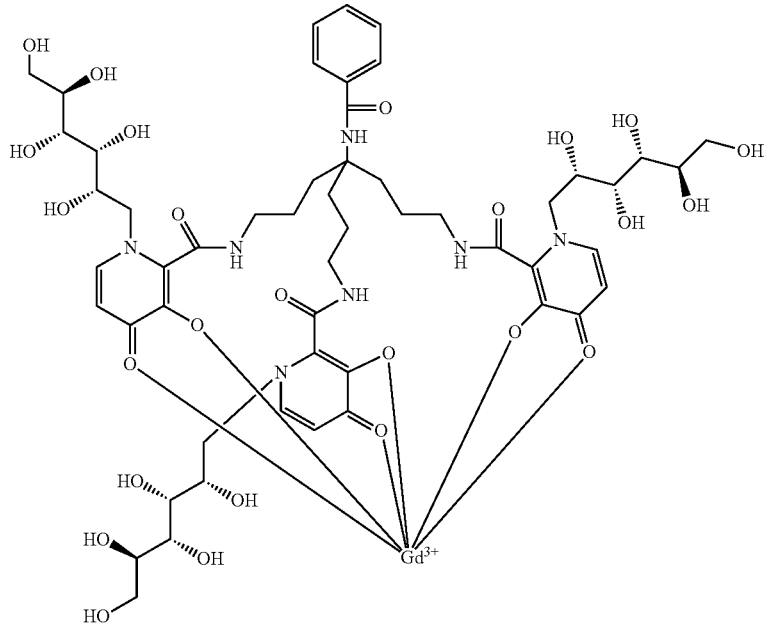

7a) Tris((3-benzyloxy-1-(2,3,4,5,6-pentahydroxy-hexyl)-4-oxo-4H-pyridinone-2-yl)-carboxyamino-propyl)-phenylcarboxyaminomethane

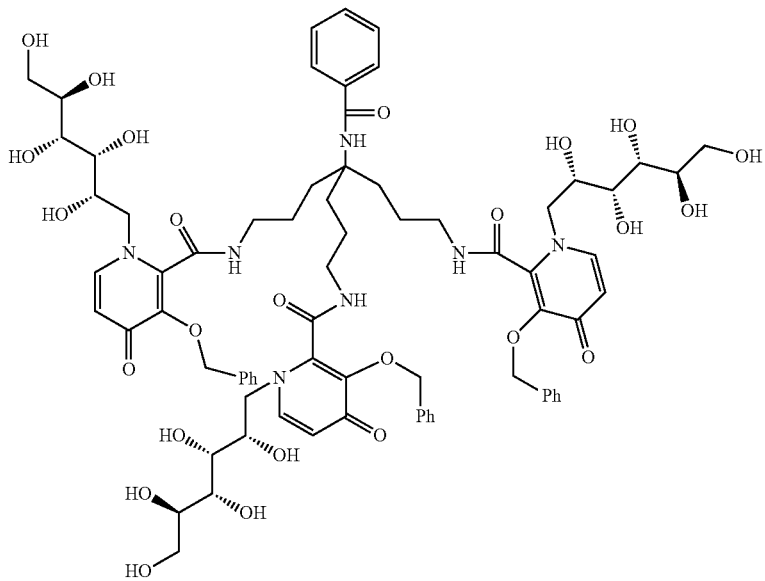

7a

A mixture of 4c (2.95 g, 3.0 mmol), D-glucamine (3.3 g, 18.2 mmol) in anhydrous methanol (90 ml) under nitrogen was heated to reflux for 4 h. LCMS indicated that heating for more than 4 h led to decomposition. The reaction mixture was concentrated in vacuo and the residue purified by column chromatography on reverse phase silica, eluting with 10-40% MeOH/H$_2$O to give impure compound 4a. The purification was repeated to afford the title compound (700 mg, 16%) as yellow crystals.

$^1$H NMR (300 MHz, DMSO) δ 1.30-1.45 (m, 6H). 1.55-1.70 (m, 6H), 3.00-3.20 (m, 6H), 3.30-4.10 (m, 24H), 4.30-4.45 (m, 6H), 4.50-4.65 (m, 6H), 4.90-5.20 (m, 9H), 6.22 (d, J=7.7 Hz, 3H), 7.15-7.80 (m, 24H), 8.75 (bt, 3H, NH).

$^{13}$C NMR (75 MHz, DMSO) δ 22.8, 32.1, 39.5, 56.4, 58.0, 63.3, 69.6, 71.3, 71.4, 72.4, 72.7, 116.6, 127.4, 127.8, 127.9, 128.1, 128.2, 130.8, 135.9, 137.7, 139.8, 140.6, 144.1, 160.6, 166.8, 172.8

LC/MS (Gemini C18 5μ 4.60×50 mm, 1 ml/min, 5-95% acetonitrile/0.1% formic acid in water/0.1% formic acid over 10 minutes) showed the material at 4.04 min m/z (ES$^+$) 1480.6 (M$^+$H).

7b) Tris((3-hydroxy-1-(2,3,4,5,6-pentahydroxy-hexyl)-4-oxo-4H-pyridinone-2-yl)-carboxyamino-propyl)-phenylcarboxyaminomethane

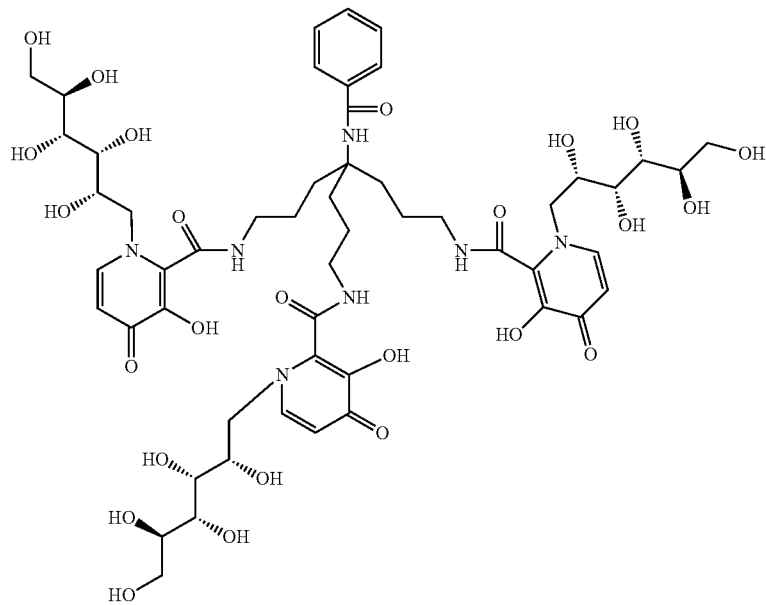

7b

To a solution of 7a (0.66 g, 0.45 mmol) in water (12 ml) and methanol (12 ml) was added palladium 10% wt on activated carbon (0.25 g). The mixture was hydrogenated at 2 bar at room temperature for 18 h. The reaction mixture was filtered through glass fibre filter paper, the paper washed with water (10 ml), methanol from the filtrate removed in vacuo and freezed-dried to afford the title compound 7b (450 mg, 83%) as a light brown solid. Note: all glassware and reaction vessels were soaked with 5 N HCl, washed with distilled water and dried in an oven to remove any potential iron contamination.

$^1$H NMR (300 MHz, D$_2$O) δ 1.50-1.70 (m, 6H). 1.75-2.00 (m, 6H), 3.30-3.50 (m, 6H), 3.50-4.40 (m, 24H), 6.42 (d, J=6.4 Hz, 3H), 7.30-7.70 (m, 8H).

$^{13}$C NMR (75 MHz, D$_2$O) δ 22.4, 32.0, 40.3, 57.8, 59.5, 62.8, 70.3, 71.1, 71.3, 72.0, 113.0 127.2, 128.8, 129.4, 132.0, 135.0, 140.5, 146.1, 162.5, 170.9, 171.4.

LC/MS (Gemini C18 5μ 4.60×50 mm, 1 ml/min, 5-95% acetonitrile/0.1% formic acid in water/0.1% formic acid over 10 minutes) showed the material at 2.02 min m/z (ES$^+$) 1210.6 (M$^+$H).

Elemental analysis: % calculated C, 49.65; H, 6.52, N, 7.65. % found C, 49.48; H, 6.26; N, 7.76. The experimental values are consistent with the presence of four water molecules, giving the new molecular formula of C$_{53}$H$_{83}$N$_7$O$_{29}$ 7) Gadolinium (III) complex of Tris((3-hydroxy-1-(2,3,4,5,6-pentahydroxyhexyl)-4-oxo-4H-pyridinone-2-yl)-carboxyaminopropyl)-phenylcarboxyaminomethane To a solution of 7b (300 mg, 0.234 mmol) in water (4 ml) was added gadolinium acetate (62.5 mg, 0.187 mmol). The reaction mixture was heated at 40° C. for 72 h, cooled and solvents removed in vacuo to give the title compound (316 mg, 99%) as a pale brown solid.

LC-MS and EA indicated approximately a 1:1 mixture of chelate and cheland. The xylenol orange sodium salt test indicated no presence of free Gd$^{3+}$.

LC/MS (Gemini C18 5μ 4.60×50 mm, 1 ml/min, 3-20% acetonitrile in water over 12 minutes) showed the product at 4.86 min m/z (ES$^+$) 1364.7 (M$^+$H) and starting material at 6.48 min m/z (ES$^+$) 1210.6 (M$^+$H).

Elemental analysis: % calculated C, 46.66; H, 5.32; N, 7.18; Gd, 11.52%. found C, 46.31; H, 5.71; N, 6.58; Gd, 6.65.

Example 8

8) Tris((3-hydroxy-1-(2,3-dihydroxypropyl)-4-oxo-4H-pyridinone-2-yl)-carboxyaminopropyl)-phenyl-carboxyaminomethane

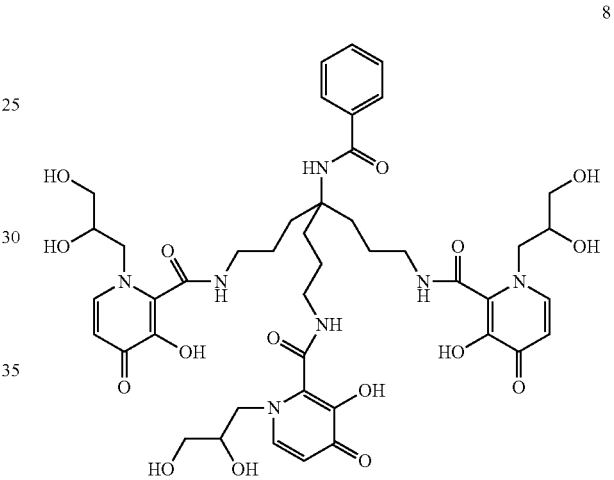

8

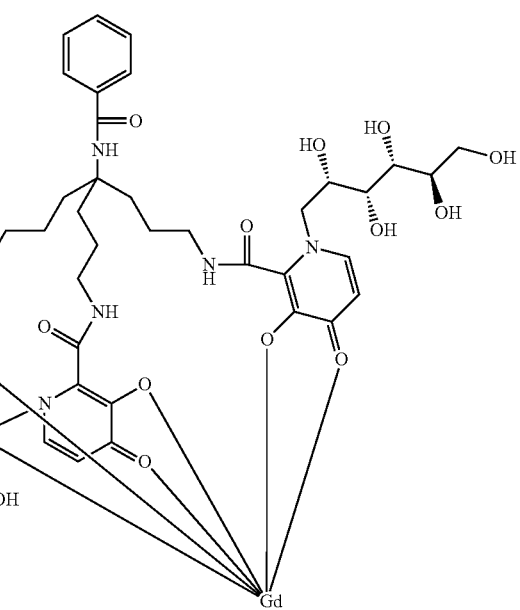

7

8a) Tris((3-benzyloxy-1-(2,3-dihydroxypropyl)-4-oxo-4H-pyridinone-2-yl)-carboxyaminopropyl)-)phenylcarboxyaminomethane    8a

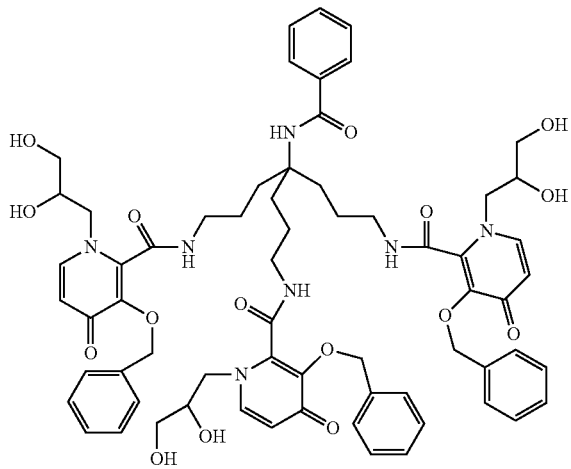

A mixture of 4c (2.6 g, 2.6 mmol), 3-amino-1,2-propanediol (1.4 g, 15.6 mmol) in anhydrous methanol (25 ml) under nitrogen was heated to reflux for 2 h. The reaction mixture was concentrated in vacuo and the residue purified by column chromatography on reverse phase silica, eluting with 60-80% MeOH/H$_2$O to give impure compound (0.9 g). The purification was repeated to afford the title compound 8a (740 mg, 24%) as a yellow solid.

$^1$H NMR (300 MHz, CD$_3$OD) δ 1.10-1.45 (m, 6H). 1.55-1.70 (m, 6H), 3.10-3.30 (m, 6H), 3.40-3.60 (m, 6H), 3.75-4.00 (m, 6H), 4.10-4.25 (m, 3H), 4.95-5.15 (m, 6H), 6.45 (d, J=7.3 Hz, 3H), 7.15-7.55 (m, 18H), 7.71 (m, 5H).

$^{13}$C NMR (75 MHz, CD$_3$OD) δ 24.0, 33.3, 41.1, 58.7, 59.9, 64.8, 72.2, 75.6, 75.7, 118.4, 128.4, 129.35, 129.41, 129.5, 129.56, 129.63, 129.7, 129.8, 132.5, 136.8, 138.30, 138.35, 142.1, 142.2, 142.6, 146.17, 146.20, 146.25, 162.7, 170.2, 175.7, 175.8

LC/MS (Gemini C18 5μ 4.60×50 mm, 1 ml/min, 5-95% acetonitrile/0.1% formic acid in water/0.1% formic acid over 10 minutes) showed the material at 4.48 min m/z (ES$^+$) 1210.7 (M$^+$H).

Note: Product chromatographed mainly as a mixture of two peaks (diastereoisomers) which give the same M$^+$H.

8) Tris((3-hydroxy-1-(2,3-dihydroxypropyl)-4-oxo-4H-pyridinone-2-yl)-carboxyaminopropyl)-phenyl-carboxyaminomethane    8

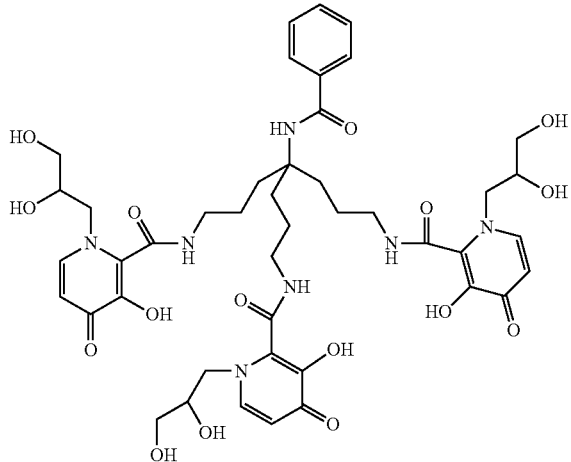

To a solution of 8a (0.74 g, 0.61 mmol) in water (10 ml) and methanol (30 ml) was added palladium 10% wt on activated carbon (0.40 g). The mixture was hydrogenated at 2 bar at room temperature for 6 h. The reaction mixture was filtered through glass fibre filter paper, the paper washed with water (10 ml), methanol from the filtrate removed in vacuo and freezed-dried to afford the title compound 8 (540 mg, 94%) as a light brown solid. Note: all glassware and reaction vessels were soaked with 5 N HCl, washed with distilled water and dried in an oven to remove any potential iron contamination.

$^1$H NMR (300 MHz, D$_2$O) δ 1.50-1.75 (m, 6H). 1.80-2.00 (m, 6H), 3.30-3.55 (m, 12H), 3.75-4.00 (m, 6H), 4.15-4.30 (m, 3H), 6.44 (d, J=7.1 Hz, 3H), 7.35-7.70 (m, 8H).

$^{13}$C NMR (75 MHz, D$_2$O) δ 22.5, 32.0, 40.3, 57.7, 59.5, 63.0, 71.0, 113.0, 127.2, 128.8, 129.5, 132.0, 135.1, 140.4, 146.0, 162.5, 170.8, 171.4

LC/MS (Gemini C18 5μ 4.60×50 mm, 1 ml/min, 5-95% acetonitrile/0.1% formic acid in water/0.1% formic acid over 6 minutes) showed the material at 2.00 min m/z (ES$^+$) 940.4 (M$^+$H).

Example 9

Synthesis of PAMAM-G1 Gadolinium Tripodal Chelate Thiourea Linked Conjugate

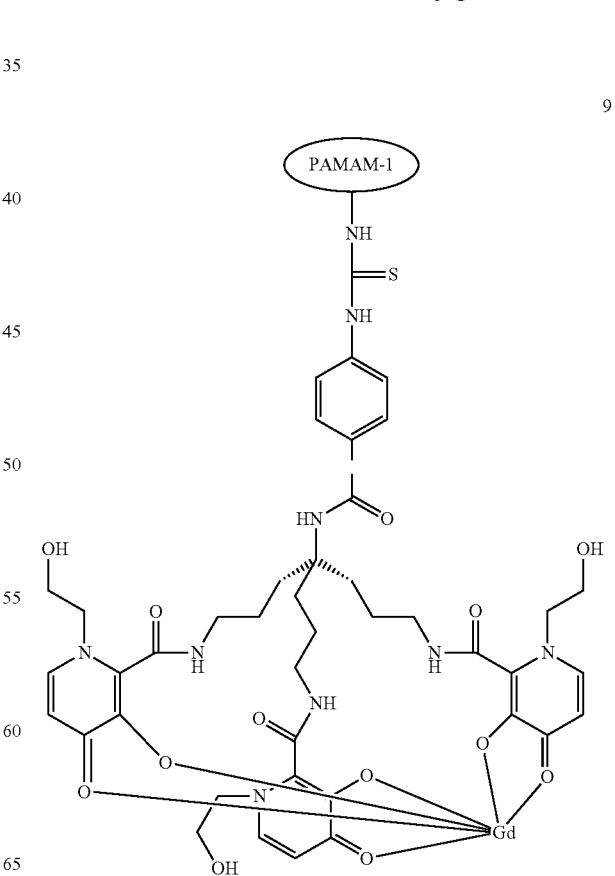

9a) Tris(3-tert-butoxycarbonylaminopropyl)-]aminomethane

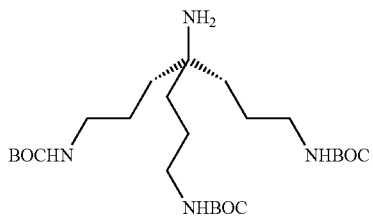

Tris(3-(tertbutoxycarbonylamino)propyl)nitromethane 1c (30 g, 59.8 mmol) and Raney-nickel (30 g) in ethanol (300 ml) was hydrogenated at 30 psi at room temperature for 18 h. The reaction was cautiously filtered through a glass fibre filter paper avoiding sucking the catalyst dry to avoid ignition. The solution was concentrated in vacuo to afford the title compound 9a (27.2 g, 87%) as a white foam.

$^1$H NMR (300 MHz, CDCl$_3$) δ 1.39 (bs, 39H), 3.05 (m, 6H), 4.73 (bs, 3H).

$^{13}$C NMR (75 MHz, CDCl$_3$) δ 24.1, 28.3, 37.0, 40.9, 52.7, 79.4, 155.9.

9b) Tris(3-Tertbutoxycarboxyaminopropyl)-p-nitrophenyl carboxyaminomethane

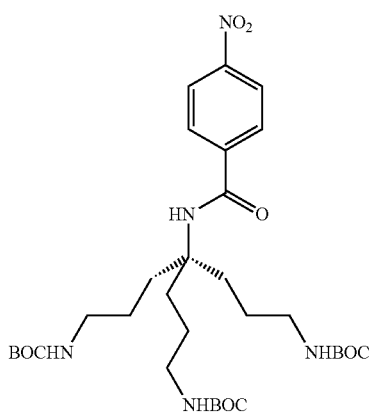

An ice cooled solution of 9a (3.0 g, 6.0 mmol) and triethylamine (0.91 g, 9.0 mmol) in dry dichloromethane (30 ml) was treated with p-nitrobenzoyl chloride (1.22 g, 6.6 mmol). The reaction mixture was stirred at room temperature for 18 h. The dichloromethane solution was washed with 10% aqueous potassium carbonate solution (20 ml), followed by water (30 ml), separated, dried over sodium sulphate and concentrated in vacuum. The residue (4.2 g) was purified by chromatography on silica with 5% methanol in dichloromethane to afford the title compound 9b (2.8 g, 72%) as a white solid.

$^1$H NMR (300 MHz, CDCl$_3$) δ 1.38, (bs, 33H), 1.77 (m, 6H), 3.08 (m, 6H), 4.77 (m, 3H, NH), 6.24 (bs, 1H, NH), 7.86 (d, J=8.9 Hz, 2H), 8.20 (d, J=8.9 Hz, 2H).

m/z (ES$^+$) 652.4 (M$^+$H).

9c) Tris(3-aminopropyl)-]p-nitrophenylcarboxyaminomethane tris trifluoroacetate salt

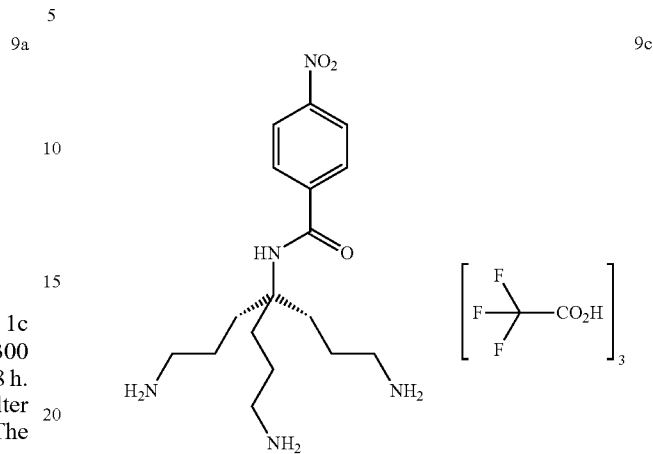

A mixture of 9b (2.8 g, 4.3 mmol) in dry dichloromethane (20 ml) was treated with TFA (20 ml) and stirred at room temperature for 24 h. The reaction mixture was concentrated in vacuum to give the title compound 9c (3.0 g, 100% yield) as a colourless oil.

$^1$H NMR (300 MHz, CD$_3$OD) δ 1.70 (m, 6H), 1.90 (m, 6H), 2.95 (m, 6H), 7.96 (d, J=8.9 Hz, 2H), 8.27 (d, J=8.9 Hz, 2H).

$^{13}$C NMR (75 MHz, CD$_3$OD) δ 22.6, 32.5, 40.9, 60.2, 124.5, 129.9, 142.3, 150.9, 168.8 m/z (ES$^+$) 352.0 (M$^+$H).

9d) Tris((3-benzyloxy-1-(2-benzyloxyethyl)-4-oxo-4H-pyridinone-2-yl)-carboxyaminopropyl)-p-nitrophenylcarboxyaminomethane

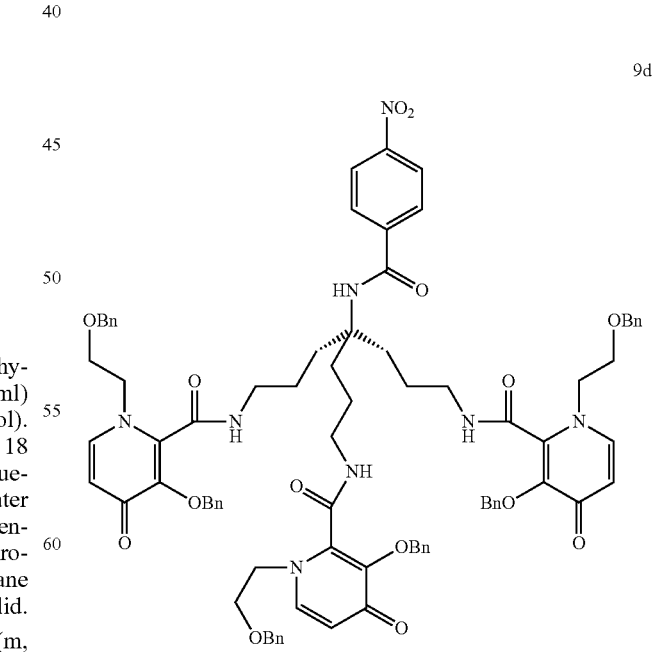

A mixture of 9c (0.94 g, 1.4 mmol) and triethylamine (0.84 g, 8.3 mmol) in dry THF (20 ml) was treated with 3-benzyloxy-1-(2-benzyloxyethyl)-pyrid-4-(1H)-one-2-carboxylic acid succinamide ester (2.0 g, 4.2 mmol) and stirred at room temperature for 24 h. Solvents were removed in vacuo, the residue partitioned between water and DCM, the aqueous layer extracted with DCM (3×30 ml), the combined organics dried over MgSO$_4$, filtered and solvents removed in vacuo to afford crude product. Chromatography on silica in a gradient of 3-30% methanol in dichloromethane gave the title compound 9d (0.68 g, 35%) as a pale yellow solid.

$^1$H NMR (300 MHz, CDCl$_3$) δ 1.18 (m, 6H). 1.49 (m, 6H), 3.08 (m, 6H), 3.73 (m, 6H), 3.94 (m, 6H), 4.43 (s, 6H), 4.93 (s, 6H), 6.09 (d, J=7.7 Hz, 3H), 6.15 (bs, 1H, NH), 7.10-7.35 (m, 34H), 7.64 (bs, 2H, NH), 7.68 (d, J=8.6 Hz, 2H), 8.03 (d, J=8.6 Hz, 2H).

$^{13}$C NMR (75 MHz, CDCl$_3$) δ 25.4, 35.0, 42.2, 57.0, 61.3, 71.3, 75.7, 77.0, 120.0, 126.1, 130.2, 130.5, 130.6, 130.8, 131.0, 139.5, 139.9, 142.2, 142.7, 143.6, 147.5, 151.7, 163.5, 167.9, 176.3 m/z (ES$^+$) 1435.7 (M$^+$H).

9e) Tris((3-hydroxy-1-(2-hydroxyethyl)-4-oxo-4H-pyridinone-2-yl)-carboxyaminopropyl)-p-aminophenylcarboxyaminomethane

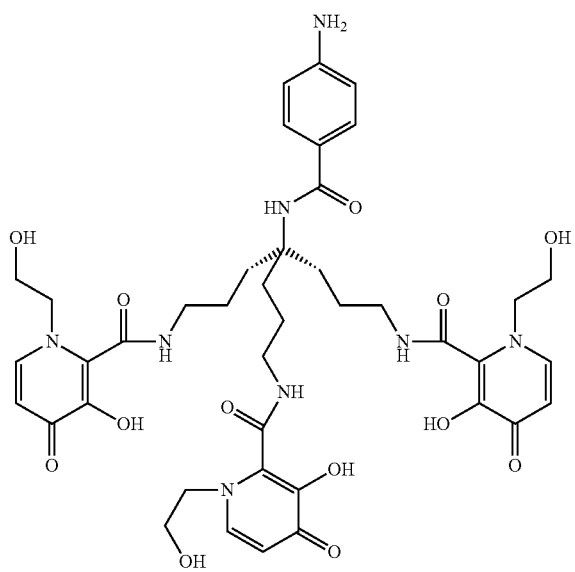

To a solution of 9d (0.50 g, 0.35 mmol) in methanol (10 ml) was added palladium 10% wt on activated carbon (0.20 g) and 6 N HCl (10 drops). The mixture was hydrogenated at 2 bar at room temperature for 18 h. The reaction mixture was filtered twice through glass fibre filter paper and solvents removed in vacuo to afford the title compound 9e (300 mg, 100%).

Note: all glassware and reaction vessels were soaked with 5 N HCl, washed with distilled water and dried in an oven to remove any potential iron contamination.

$^1$H NMR (300 MHz, CD$_3$OD) δ 1.70 (m, 6H). 1.97 (m, 6H), 3.47 (m, 6H), 3.90 (m, 6H), 4.44 (m, 6H), 7.24 (d, J=6.5 Hz, 3H), 7.50 (d, J=8.3 Hz, 2H), 7.93 (d, J=8.3 Hz, 2H), 8.22 (d, J=6.5 Hz, 3H).

$^{13}$C NMR (75 MHz, CD$_3$OD) δ 24.1, 33.6, 41.4, 60.5, 60.8, 61.5, 112.5, 124.3, 130.4, 134.6, 137.7, 138.1, 141.2, 145.0, 160.9, 162.4, 169.0 m/z (ES$^+$) 865.4 (M$^+$H).

9f) Tris((3-hydroxy-1-(2-hydroxyethyl)-4-oxo-4H-pyridinone-2-yl)-carboxyaminopropyl)-p-isothiocyanatophenylcarboxyaminomethane

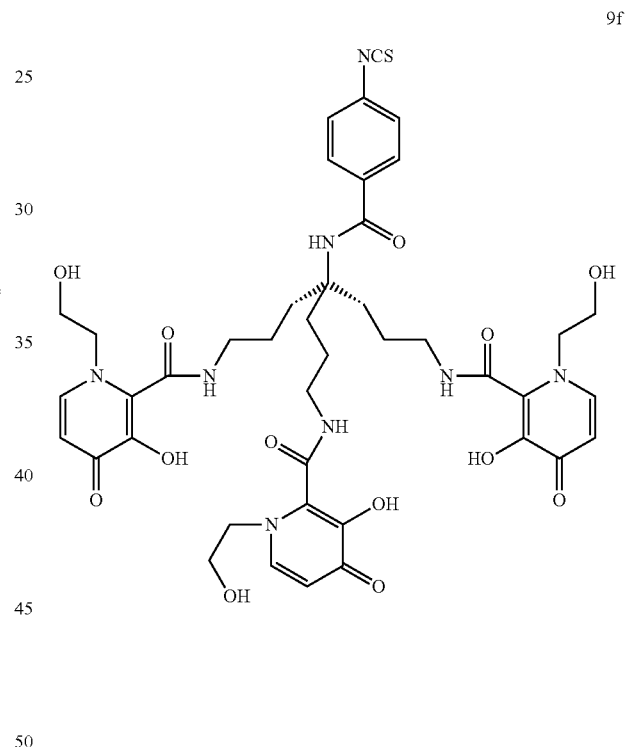

To an ice cooled solution of 9e (200 mg, 0.23 mmol) in water (2 ml) and dioxane (2 ml) was added thiophosgene (32 mg, 0.28 mmol). The orange-red solution was stirred at room temperature for 2 h. The solvents removed in vacuo and freezed-dried to afford the title compound 9f (200 mg, 95%) as a pale yellow solid.

$^1$H NMR (300 MHz, CD$_3$OD) δ 1.69 (m, 6H). 1.96 (m, 6H), 3.45 (m, 6H), 3.89 (m, 6H), 4.43 (m, 6H), 7.24 (d, J=6.4 Hz, 3H), 7.33 (d, J=8.0 Hz, 2H), 7.80 (d, J=8.0 Hz, 2H), 8.22 (d, J=6.4 Hz, 3H).

$^{13}$C NMR (75 MHz, CD$_3$OD) δ 24.1, 33.6, 41.4, 60.5, 60.8, 61.5, 112.6, 126.6, 130.2, 135.2, 135.7, 138.1, 138.5, 141.2, 145.0, 160.8, 162.4, 169.0 m/z (ES$^+$) 907.4 (M$^+$H).

9g PAMAM-G1 Tripodal Chelate Thiourea Linked Conjugate

| ELEMENT | C | H | N | S | Fe | Na |
|---|---|---|---|---|---|---|
| % Theory | 55.04 | 6.13 | 14.51 | 2.95 | | |
| % Found 1 | 51.52 | 6.21 | 12.82 | 2.29 | 0.03 | 0.54 |
| % Found 2 | 51.55 | 6.22 | 12.86 | 2.34 | 0.02 | 0.46 |

9) PAMAM-G1 Gadolinium Tripodal Chelate Thiourea Linked Conjugate

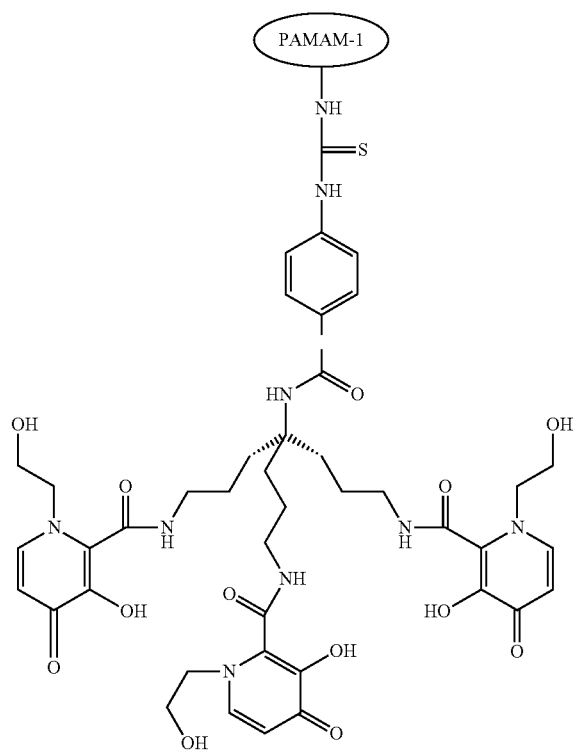

9g

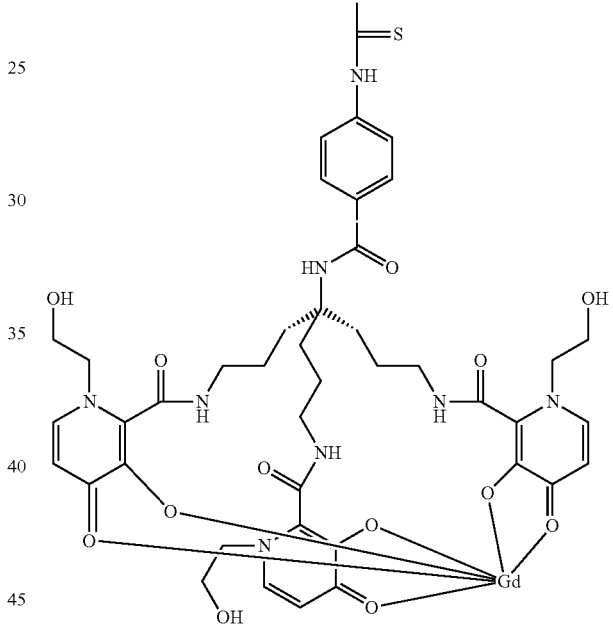

9

A solution of PAMAM G1 (208 µl) of 20% solution in methanol, 41 mg dry weight of dendrimer, 0.028 mmol primary amines) in water (3 ml) was treated with 9f (8 eq, 200 mg, 0.22 mmol) in THF (1 ml). The pH was adjusted to 9 with 1.5 M sodium hydroxide and the solution stirred at 40° C. for 24 h. Then, an additional 50% molar excess of 9f (4 eq, 100 mg, 0.11 mmol) was added, pH was readjusted to 9 with 1.5 M sodium hydroxide, and the mixture was stirred at 40° C. for an additional 24 h. Subsequently, the pH was adjusted to 7 by addition of concentrated hydrochloric acid and solvents removed in vacuo to afford a brown solid. The solid was dissolved in 50% ethanol/water (10 ml), filtered and solvents removed in vacuo. The residue was re-dissolved in 50% ethanol/water (15 ml) with heat and purification attempted using Centriprep centrifugal filter device. For G1 conjugate, membrane YM3 (cutoff at 3 kDa) was used. Sample was centrifuged in a Rotina 35R Hettich Zentrifugen at 3000 g in a swinging-bucket at 25° C. The sample volume could only be reduced from 15 ml to 10 ml using two spin cycles. Spin #1 (100 min), spin #2 (100 min) adding water (5 ml) to the retentate and gently agitating the mixture between each spin cycle. The retentate was diluted with methanol (10 ml), filtered, to afford the title compound 9 (35 mg) as a light brown solid.

EA: Formula $C_{254}H_{400}N_{74}O_{68}S_8$

PAMAM-G1 tripodal chelate thiourea conjugate 9f (30 mg, 5.1 nmol) in water (1 ml) was treated with gadolinium acetate (13.7 mg, 40.5 nmol) and the reaction stirred at room temperature overnight. The reaction was then purified using a Centriprep centrifugal filter device using a YM3 (cutoff at 3 kDa) membrane in a swinging-bucket Rotina 35R Hettich Zentrifugen centrifuge at 3000 g. at 25° C. to remove any unbound gadolinium. The sample volume was reduced from 15 ml to 10 ml on each spin cycles of 100 min, water (5 ml) was added to the retentate and this was gently agitated before beginning the next spin cycle. This procedure was repeated 6 times and the resulting solution was then freeze dried to give the title compound 9 as a slightly yellow solid (35 mg, 4 nmol).

Example 10

PAMAM-G2 Gadolinium Tripodal Chelate Triazole Linked Conjugate

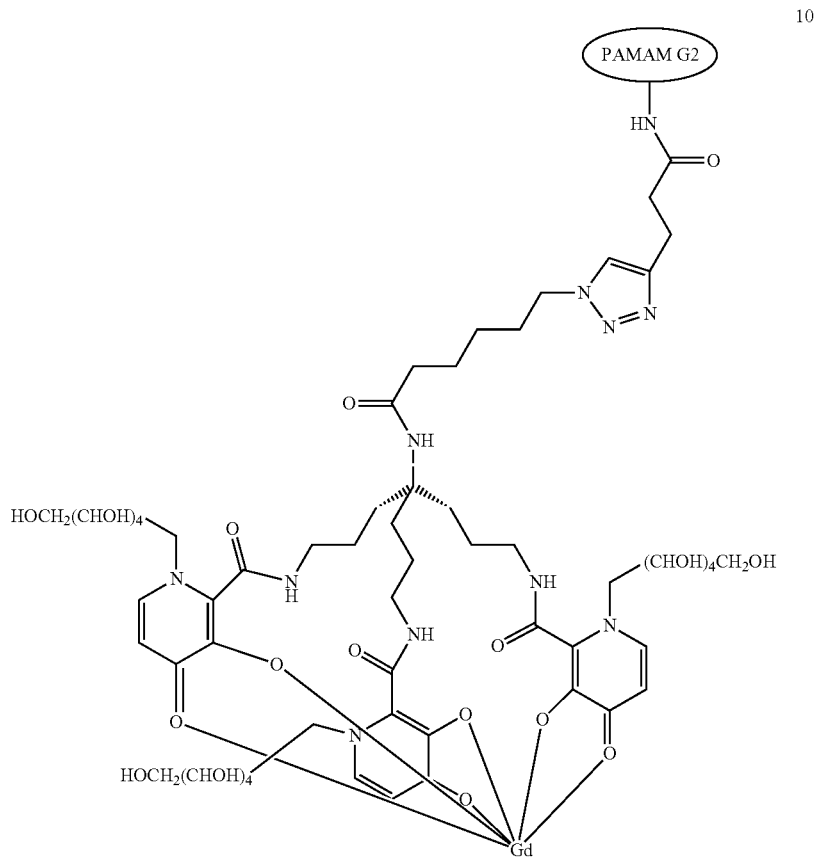

10a) Pent-4-ynoic acid 2,5-dioxo-pyrrolidin-1-yl ester

10b) Pent-4-ynoic acid PAMAM G2 amide

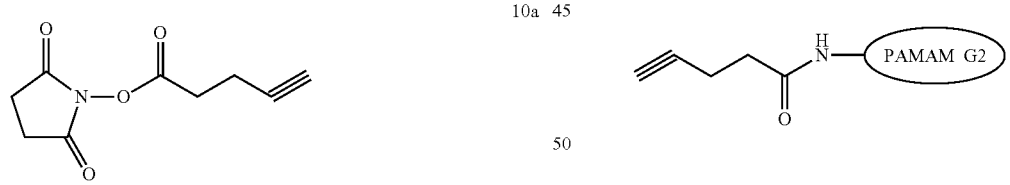

4-pentynoic acid (5.0 g, 51 mmol) and N-hydroxy succinimide (5.87 g, 51 mmol) were added to a solution of DCC (12.6 g, 61.2 mmol) in THF (125 ml) at −10° C. The mixture was then stirred for 1 h at −10° C. then left to stir at room temperature overnight. (A white precipitate was observed after 15 min). Acetic acid (0.63 ml) was then added. The resulting DCU was removed by filtration. The filtrate was then evaporated to give 10a (10 g, 100% crude yield).

$^1$H NMR (300 MHz; DMSO-$d_6$) δ 2.53 (dt, $J_{HH}$ 7 Hz, $J_{HH}$ 3 Hz, 2H, CH$_2$), 2.76-2.86 (m, 7H, CH$_2$×2, CH×3), 2.91 (t, $J_{HH}$ 7 Hz, 2H, CH$_2$).
$^{13}$C NMR (75 MHz; DMSO-$d_6$) δ 13.5 (CH$_2$), 25.5 (CH$_2$× 2), 29.7 (CH$_2$), 71.9 (CH), 82.0 (CH), 167.7 (C═O), 170.2 (C═O×2).

Pent-4-ynoic acid 2,5-dioxo-pyrrolidin-1-yl ester 10a (1.219 g, 6.25 mmol) in dry THF (20 ml) was added slowly to PAMAN G2 20% solution in methanol (5 ml, 5 mmole of amino groups) diluted in dry THF (20 ml) with stirring and then heated to reflux for 2 h. The reaction was then concentrated in vacuum to a gum and this was stirred with ethyl acetate. There was an immediate heavy precipitate formed that was collected by filtration. The solid collected was a colourless powder that was extremely hydroscopic. The solid was dissolved in water and filtered and purified by microfiltration to remove low molecular weight impurities. Half of the 15 ml of aqueous solution was forced through a micro pore filter using a centrifuge. The liquid that passed through the centrifuge was discarded whilst the remaining liquid was diluted with water to 15 ml and the process repeated 6 times. The aqueous solution after micro filtration was freeze dried to give a colourless solid. NMR run in $CD_3OD$ gave two pairs of peaks that were assigned to acetylene CH and C signals. It was assumed that these signals were due to the presence of acetylene attached to the PAMAM via an amide bond and attached to the PAMAM as a salt. The pentyanoic acid salt was removed by treating the acetylene PAMAN with sodium acetate (2.5 g in water 10 ml) stirring for 10 minutes. The solution was then subjected to six cycles of mimicrofiltration as described above to remove the sodium acetate and any released sodium pentyanoate. (The non covalently bound acetylene). The aqueous solution was then freeze dried to give a solid glass 10b. Weight 1.5067 g. Yield 108%. Slightly wet and acetate salt.

Results: $^1H$ and $^{13}C$ NMR in $CD_3OD$ indicated correct structure.

Conclusion: Yield probably about 100% but difficult to quantify as water and salts impossible to remove.

PAMAN G2 $COCH_2CH_2$—C≡CH

Formula $C_{222}H_{352}N_{58}O_{44}$ MWt=4532. 16 acetylene groups per molecule.

10c) Tris(3-aminopropyl)nitromethane trifluoroacetate salt

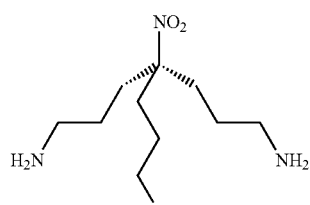

Tris. trifluoroacetate salt

A mixture of tris(3-(tert-butoxycarbonylamino)propyl)nitromethane 1c (10 g, 18.8 mmol) in trifluoroacetic acid (20 ml) and dichloromethane (50 ml) was stirred at room temperature for 4 h. The reaction was then concentrated under high vacuum to afford the title compound 10c (10.8 g, 18.8 mmol. 100%) as a gum.

$^1H$ NMR (300 MHz; $CD_3OD$) δ 1.55-1.71 (m, 6H, $CH_2$×3), 2.01-2.07 (m, 6H, $CH_2$×3), 2.96 (t, $J_{HH}$ 6 Hz, $CH_2$×3), 5.02 (s, 9H, $^+NH_3$×3).

$^{13}C$ NMR (75 MHz; $CD_3OD$) δ 22.9 ($CH_2$×3), 33.2 ($CH_2$×3), 40.3 ($CH_2$×3), 94.2 (C—$NO_2$), 161.8 ($J_{CF}$ 147 Hz, $CF_3$$\underline{C}O_2H$).

10d Tris((3-benzyloxy-4-oxo-4H-pyran-2-yl)carboxyaminopropyl))nitromethane

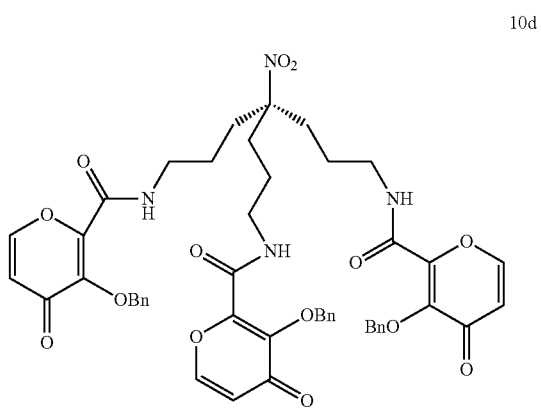

A mixture of tris(3-aminopropyl)nitromethane trifluoroacetate salt 2d (5.39 g, 9.40 mmol) in THF (100 ml) was treated with N-hydroxy succinimidyl-3-benzyloxy-4-oxo-4-H-pyran-2-carboxylate (S. M. Cohen, D. T. Puerta, and K. N. Raymond, *J. Amer. Chem. Soc.* 2006, 128, 2222.) (11.3 g, 32.9 mmol) and triethylamine (18 ml, 131 mmol) with stirring at room temperature for 18 h. The reaction was then concentrated in vacuo to a gum and re-dissolved in dichloromethane (100 ml). The solution was washed with 10% aqueous potassium carbonate solution dried over sodium sulfate and concentrated under high vacuum to a gum. The product was then purified by flash chromatography using a 330 g silica column with a gradient of 3-10% methanol in dichloromethane. The main UV active fraction was collected, and concentrated in high vacuum to afford the title compound 2e as a gum. (5.18 g, 60%).

$^1H$ NMR (300 MHz; $CDCl_3$) δ 1.07-1.21 (m, 6H, $CH_2$×3), 1.62-1.72 (m, 6H, $CH_2$×3), 3.14 (m, 6H, $CH_2$×3), 5.39 (s, 6H, $OCH_2$×3), 6.47 (d, $J_{HH}$ 8 Hz, CH×3), 7.38 (s, 15H, ArCH×5), 7.70 (br t, 3H, NH×3), 7.81 (d, $J_{HH}$ 8 Hz, 3H, CH×3).

$^{13}C$ NMR (75 MHz) δ 23.4 ($CH_2$×3), 32.6 ($CH_2$×3), 39.3 ($CH_2$×3), 93.1 (C—$NO_2$), 117.6 (CH×3), 129.0 (ArCH×6), 129.1 (ArCH×6), 129.4 (ArCH×3), 135.4 (ArC), 146.7 (C—CO×3), 147.3 (ArCH×3), 154.6 (C—O×3), 159.0 (C=O×3), 175.6 (C=O×3).

10e) Tris((3-benzyloxy-1-(2,3,4,5,6-pentahydroxy-n-hexane)-4-oxo-4H-4-pyridone-2-yl)carboxyamino propyl))nitromethane

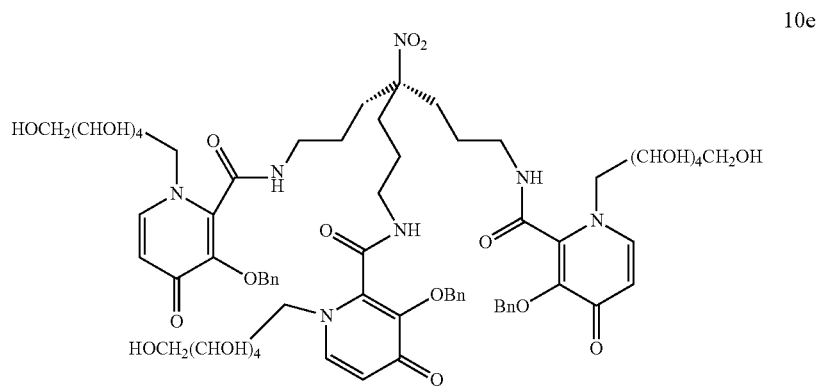

10e

D-Glucamine (1.58 g, 8.72 mmol) was added to a stirred solution of 10d (1.0 g, 1.09 mmol) in methanol (50 ml). The resulting suspension was then heated under reflux (heater read 96° C.) for 2 h. D-glucamine slowly dissolved over 1 h. The reaction was monitored by LCMS. After 2 h LCMS showed starting material and mono and di byproducts had gone. The solvent was removed under reduced pressure to afford a yellow oil. This was then dissolved in water and then purified by reverse phase chromatography. To give 10e as a gum (628 mg 44 mmol, 41%).

$^1$H NMR (300 MHz; CDCl$_3$) δ 1.22 (m, 6H, CH$_2$×3), 1.65 (m, 6H, CH$_2$×3), 3.05-4.10 (m, 30H, NHCH$_2$×3, CH—OH×12, OCH$_2$ (Bn)×3, CH$_2$N×3), 4.40 (br s, 6H, OH×6), 4.57 (br s, 6H, OH×6), 4.98-5.55 (m, 9H, OH×3, CH$_2$OH×3), 6.23 (d, $J_{HH}$ 8 Hz, 3H, CH×3), 7.41-7.50 (m, 15H, ArCH×15), 7.54 (d, $J_{HH}$ 8 Hz, 3H, CH×3), 8.78 (br t, 3H, NH×3).

$^{13}$C NMR (75 MHz; DMSO-d$_6$) δ 22.9 (CH$_2$×3), 32.5 (CH$_2$×3), 40.0 (CH$_2$×3), 56.3 (CH$_2$×3), 63.2 (OCH$_2$×3), 69.6 (C—OH), 71.2 (C—OH), 71.4 (C—OH), 72.3 (C—OH), 72.6 (CH$_2$OAr), 93.6 (C—NO$_2$), 116.5 (CH×3), 127.8 (ArCH×8), 128.2 (ArCH×7), 137.6 (CH×3), 139.5 (ArC), 140.6 (N—C=O—C), 144.1 (C=O×3), 160.7 (C=O×3), 172.7 (C=O×3).

(ES$^+$) m/z 1406.7 (M), 704.04 (M+2/2)

10f) Tris((3-benzyloxy-1-(2,3,4,5,6-pentahydroxy-n-hexane)-4-oxo-4H-4-pyridone-2-yl)carboxyamino propyl))methylamine

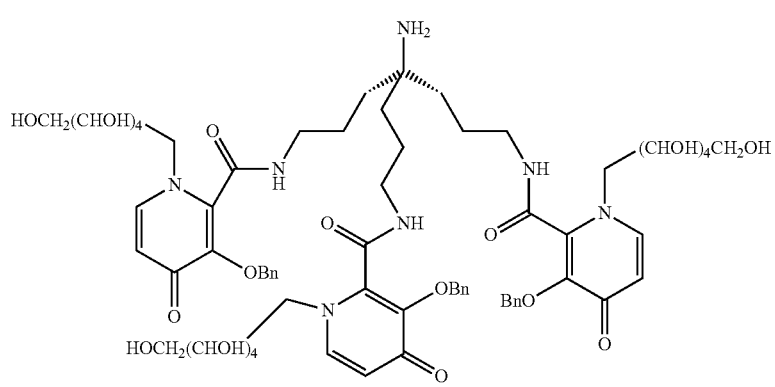

10f 10e (2.17 g, 1.54 mmol) and Raney nickel (4 g) was dissolved in a mixture of 50:50 water/methanol (80 ml). The mixture was then left to shake at room temperature overnight. LCMS showed the reaction was not complete and also the hydroxylamine intermediate was seen. The reaction was left for a further 3 days at room temperature. LCMS indicated that the reaction was complete. The mixture was passed through celite. The filtrate was then evaporated to dryness to afford 10f as a bright orange foam (1.55 g, 73%)

$^1$H NMR (300 MHz; DMSO-d$_6$) δ 1.10 (m, 6H, CH$_2$×3), 1.33 (m, 12H, CH$_2$×6), 3.11-5.65 (m, 49H, NH$_2$, NCH$_2$×3, 12×CH—OH, OCH$_2$×3, OCH$_2$×3, 15×OH) (broad signals)

$^{13}$C NMR (75 MHz; DMSO-d$_6$) δ 23.0 (CH$_2$×3), 36.5 (CH$_2$×3), 56.3 (CH$_2$×3), 63.2 (OCH$_2$), 69.5 (C—OH), 71.3 (2×C—OH), 72.4 (C—OH), 72.6 (OCH$_2$×3), 116.5 (CH×3), 127.7 (ArCH×3), 128.1 (ArCH×2), 137.8 (C), 139.7 (C), 140.5 (CH×3), 144.1 (C—O×3), 160.6 (C=O×3), 172.8 (C=O×3).

(ES$^+$) m/z 1376 (M) 688 (M+2/2)

10g) Tris(3-benzyloxy-1-(2,3,4,5,6-pentahydroxy-n-hexane)-4-oxo-4H-4-pyridone-2-yl)carboxyamino propyl) 6-bromohexanoic acid methylamide 6-bromohexanoyl chloride (0.13 ml, 0.82 mmol) was added to 10f (1.03 g, 0.75 mmol) and triethylamine (0.11 ml, 0.82 mmol) in DMF (120 ml) at −70° C. The mixture was allowed to reach room temperature and stirred for 18 h. LCMS indicated that the desired material had been formed as a single product. A sample was concentrated in vacuum and analysed by 13C NMR. This indicated that the desired product 10g had been formed. The bulk reaction mixture in DMF was then taken to the next (azide displacement) stage without work-up. Yield assumed to be quantitative.

$^{13}$C NMR (75 MHz; DMSO-d$_6$) δ 22.3 (CH$_2$×3), 23.9 (CH$_2$), 24.2 (CH$_2$), 23.5 (CH$_2$), 32.6 (CH$_2$), 34.5 (CH$_2$×3), 44.7 (CH$_2$), 56.4 (CH$_2$×3), 56.5 (C), 63.2 (OCH$_2$×3), 69.5 (CH), 71.3 (CHOH×3), 71.4 (CHOH×3), 72.4 (CHOH×3), 72.7 (CHOH×3), 116.5 (CH×3), 127.8 (ArCH×2), 128.2 (ArCH×2), 137.7 ( ), 139.8 ( ), 140.6 (CH×3), 144.1 (C—O× 3), 160.6 (C=O×3), 172.0 (C=O×3), 172.8 (C=O×3).

(ES$^+$) m/z 1554.7 (M), 777.1 (M+2/2) product

IR (neat): 1100.00, 1243.48, 1386.96, 1552.17, 1617.39, 1647.83 cm$^{-1}$

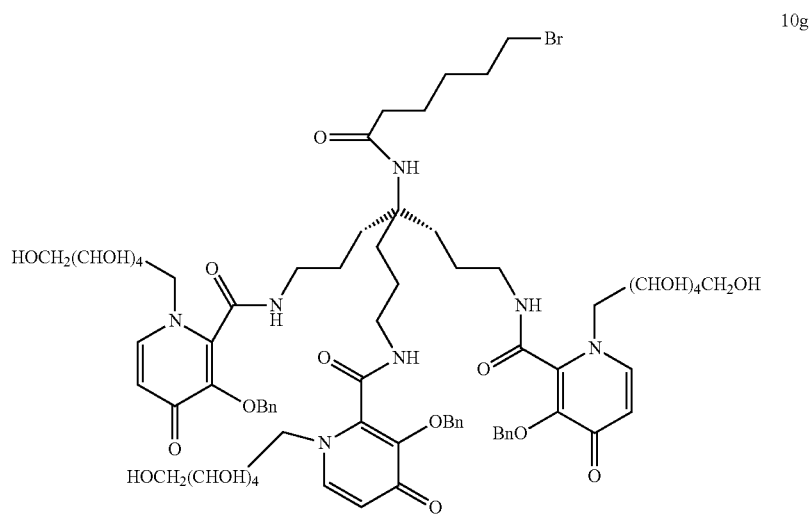

10h) Tris(3-benzyloxy-1-(2,3,4,5,6-pentahydroxy-n-hexane)-4-oxo-4H-4-pyridone-2-yl)carboxyamino propyl) 6-azido hexanoic acid methylamide

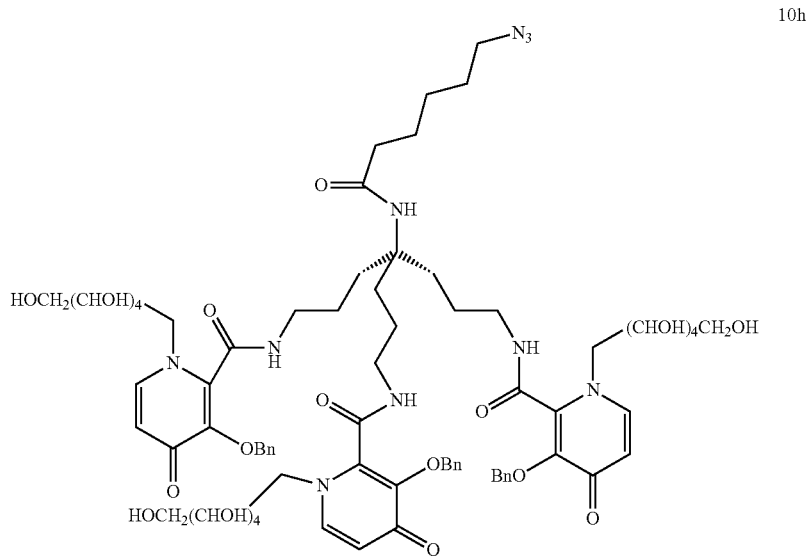

Sodium azide (97 mg, 1.49 mmol) was added to crude reaction mixture of 10g (1.16 g, 0.75 mmol) in DMF (120 ml). The reaction was then stirred at room temperature for 72 h. After which time LCMS indicated that a product with the correct mass had been formed. The solvents were removed in vacuo to afford the crude product as an orange solid 2.42 g (hygroscopic). The material was then purified using reverse phase chromatography. The compound was dissolved in a 50:50 mixture of methanol:water. The eluent began with 50:50 methanol:water then after 10 fractions the percentage of methanol was increased by 5%. 10h was collected at ca. 55%-60% methanol and was obtained as a pale orange oil (0.38 g, 34%).

$^1$H NMR (300 MHz, DMSO-$d_6$) δ 1.15-1.60 (m, 18H, CH$_2$×3, CH$_2$×3, CH$_2$, CH$_2$, CH$_2$), 2.01 (m, 2H, CH$_2$), 3.09-4.12 (m, 32H, CHOH×12, CH$_2$×3, CH$_2$N$_3$, OCH$_2$×3, CH$_2$N×3), 4.52 (br s, 6H, OH×6), 4.74 (br s, 6H, OH×6), 5.05 (m, 6H, CH$_2$OH×3), 5.27 (br s, 3H, OH×3), 6.22 (d, J$_{HH}$ 7 Hz, 3H, CH), 6.93 (br s, 0.5H, NH), 7.25-7.48 (m, 15H, ArCH×15), 7.58 (d, J$_{HH}$ 7 Hz, 3H, CH), 8.38 (br s, 0.5H, NH), 8.81 (br s, 3H, NH×3).

$^{13}$C NMR (75 MHz, DMSO-$d_6$) δ 23.2 (CH$_2$×3), 23.9 (CH$_2$), 25.5 (CH$_2$), 26.0 (CH$_2$), 26.4 (CH$_2$), 28.5 (CH$_2$), 28.6 (CH$_2$), 29.5 (CH$_2$), 32.6 (CH$_2$×3), 36.5 (CH$_2$), 40.5 (CH$_2$×3), 49.2 (CH$_2$), 51.0 (CH$_2$), 51.1 (CH$_2$N$_3$), 51.7 (CH$_2$N$_3$), 56.9 (NCH$_2$×3), 57.6 (C—NHCO), 63.8 (OCH$_2$×3), 70.0 (CHOH×3), 71.9 (CHOH×3), 72.0 (CHOH×3), 73.1 (CHOH×3), 73.2 (OCH$_2$×3), 117.1 (CH×3), 128.7 (ArCH×7), 128.8 (ArCH×6), 138.3 (ArC), 140.3 (ArC), 141.1 (CH), 144.6 (C—O×3), 161.2 (C=O×3), 172.5 (C=O), 173.3 (C=O×3).

(ES$^+$): m/z 1515.71 (M), 759.12 (M+2/2)
IR (neat): 2095.7, 2039.1, 1656.5, 1613.0, 1556.5, 1247.8 cm$^{-1}$

10i) PAMAM-G2 Tripodal Chelate Triazole Linked Conjugate Benzyl Protected

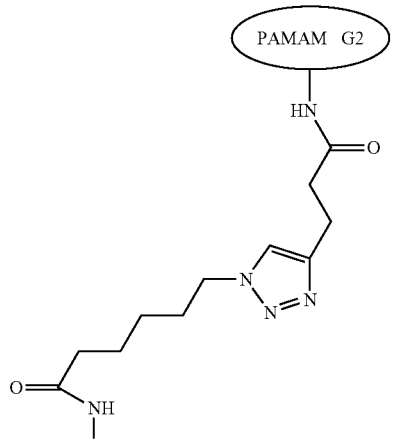

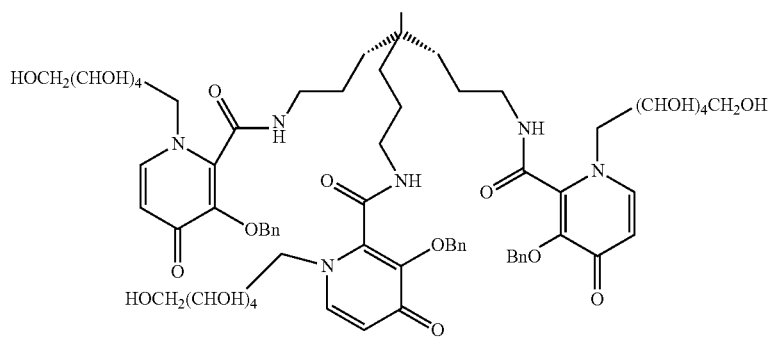

Pamam G2 pentynoic acid amide 10b (31 mg, 0.112 mmol of acetylene in water (1 ml) was stirred with 21 Tris(3-benzyloxy-1-(2,3,4,5,6-pentahydroxy-n-hexane)-4-oxo-4H-4-pyridone-2-yl)carboxyamino propyl) 6-azido hexanoic acid methylamide, copper II sulphate (3 mg, 11.2 nM) and 1-ascorbic acid (2 mg, 11.2 nmol) and adjusted to pH 7 with aq sodium hydroxide. The reaction was then subjected to six cycles of microfiltration as described in example 9 to remove any unreacted low molecular weight material. The solution was then freeze dried to give an off white powder 10i (74.5 mg).

10j) PAMAM-G2 Tripodal Chelate Triazole Linked Conjugate

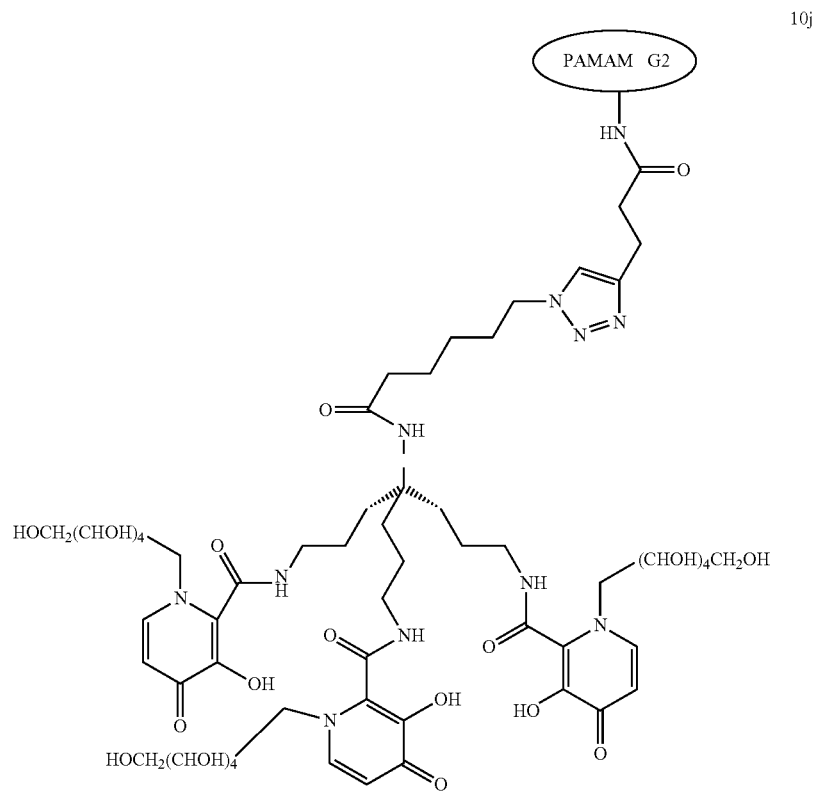

10i PAMAM-G2 tripodal chelate thiourea linked conjugate benzyl protected (50 mg) was dissolved in methanol (10 ml) and treated with 10% palladium on charcoal under an atmosphere of hydrogen for 18 h. The reaction was then filtered through celite to remove the catalyst. The filtrate was then concentrated in vaccuo to give the desired compound 10j as a gum.

10 PAMAM-G2 Gadolinium Tripodal Chelate Triazole Linked Conjugate

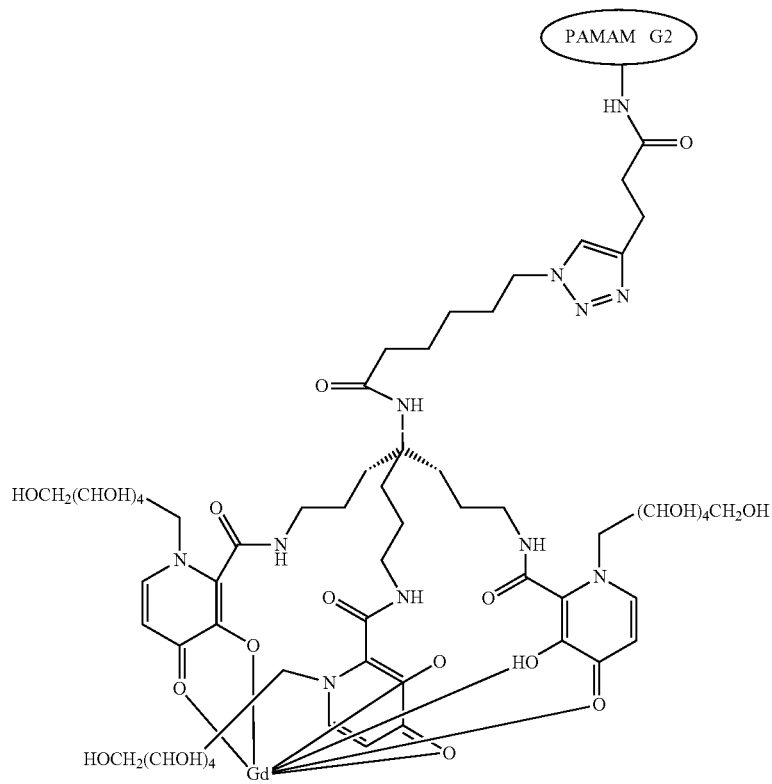

10j PAMAM-G2 tripodal chelate thiourea linked conjugate (40 mg) was dissolved in water (1 ml) and treated with gadolinium acetate (20 mg). The reaction was then stirred at room temperature overnight and then subjected to six cycles of microfiltration as described in example 9. The reaction was then freeze dried to give the title compound as a yellow powder (40 mg).

What is claimed is:

1. Compound of formula (I):

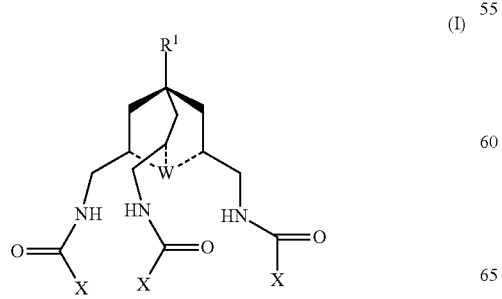

wherein $R^1$ is H, $NO_2$, $NH_2$ or $NHC(=O)R^2$, wherein $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$ wherein n is 0 to 6 and m is 1 to 6;

W and the bonds represented as dotted lines are present or absent and when present, W is N; and wherein when W is not present, $R^1$ is NHC(O)$R^2$, wherein $R^2$ is $C_7$-$C_{22}$-arylalkyl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$;

X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions.

2. Compound according to claim 1 further comprising a paramagnetic metal ion M to form a compound of formula (II):

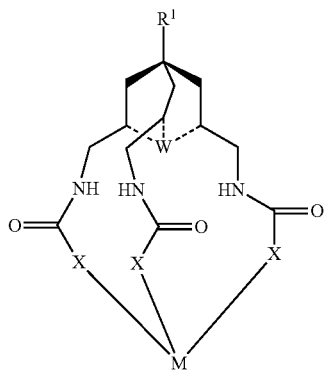

(II)

wherein $R^1$, W and X are as defined in claim 1 and M is a paramagnetic metal ion.

3. Compound according to claim 1 wherein X is derived from hydroxypyrones, dihydroxypyridines, hydroxypyrimidones, hydroxypyridones, hydroxy-pyridinones and dihydroxyphenols.

4. Compound according to claim 2 wherein M is a paramagnetic metal ion of Mn, Fe, La, Co, Ni, Eu, Gd, Dy, Tm or Yb.

5. Compound according to claim 1 wherein $R^1$ is H or NHC(=O)$R^2$, wherein $R^2$ is $C_1$-$C_6$-alkyl, $C_6$-$C_{15}$-aryl, $C_7$-$C_{22}$-arylalkyl, O—$C_1$-$C_6$-alkyl or O—$C_7$-$C_{22}$-arylalkyl.

6. Compound of formula (I):

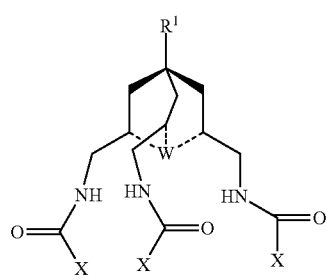

(I)

wherein $R^1$ is NHC(=O)$R^2$, wherein $R^2$ is $(CH_2)_n$—$(C_6H_4)$—NCS, $(CH_2)_m$—C≡CH or $(CH_2)_m$—$N_3$ wherein n is 0 to 6 and m is 1 to 6;

W and the bonds represented as dotted lines are present or absent and when present, W is N; and X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions.

7. Compound according to claim 1 linked to another molecule via the $R^1$-group.

8. Compound according to claim 7 wherein said another molecule is a natural or synthetic peptide, a peptidomimetic, a polypeptide, a protein, an antibody, a natural or synthetic polymer, a dendrimer, a nanoparticle or a lipophilic compound.

9. Compound of formula (I):

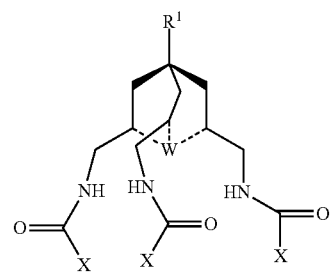

(I)

wherein $R^1$ is NHC(=O)$R^2$ and $R^2$ is $(CH_2)_n$—$(C_6H_4)$—NCS and n is 0 to 6;

W and the bonds represented as dotted lines are present or absent and when present, W is N; and X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions;

wherein said compound of formula (I) is linked to another molecule via the $R^1$-group and said another molecule comprises an amino group and is selected from a polypeptide, a protein, an antibody, a natural or synthetic polymer and a dendrimer and wherein said compound of formula (I) is linked to said another molecule via a thiourea bond formed by a reaction of the $R^1$-group of compound of formula (I) with said amino groups of said another molecule.

10. Compound of formula (I):

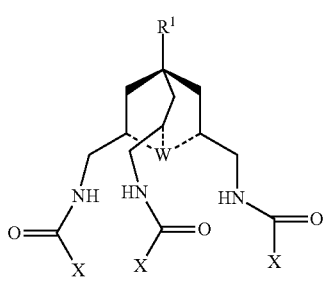

wherein
R$^1$ is NHC(=O)R$^2$ and R$^2$ is (CH$_2$)$_m$—C≡CH and m is 1 to 6;
W and the bonds represented as dotted lines are present or absent and when present, W is N; and
X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions;
wherein said compound of formula (I) is linked to another molecule via the R$^1$-group and wherein said another molecule comprises an azido group and is selected from a polypeptide, a protein, an antibody, a natural or synthetic polymer and a dendrimer and wherein said compound of formula (I) is linked to said another molecule via a 1,2,3-triazole ring formed by a reaction of the R$^1$-group of compound of formula (I) with said azido groups of said another molecule.

11. Compound of formula (I):

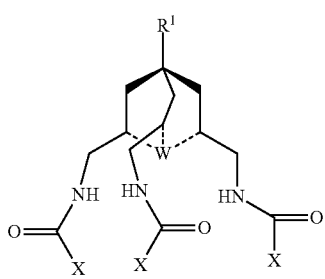

wherein
R$^1$ is NHC(=O)R$^2$ and R$^2$ is (CH$_2$)$_m$—N$_3$ and m is 1 to 6;
W and the bonds represented as dotted lines are present or absent and when present, W is N; and
X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions;
wherein said compound of formula (I) is linked to another molecule via the R$^1$-group and wherein said another molecule comprises an ethynyl group and is selected from a polypeptide, a protein, an antibody, a natural or synthetic polymer and a dendrimer and wherein said compound of formula (I) is linked to said another molecule via a 1,2,3-triazole ring formed by a reaction of the R$^1$-group of compound of formula (I) with said ethynyl groups of said another molecule.

12. Composition comprising a compound according to claim 2 and at least one physiologically tolerable carrier.

13. Method of MR imaging wherein a composition according to claim 12 is administered to a subject and the subject is subjected to an MR examination wherein MR signals are detected from the subject or parts of the subject into which the composition distributes and optionally MR images and/or MR spectra are generated from the detected signals.

14. Method for producing a compound of formula (I) wherein R$^1$ is NHC(=O)R$^2$ and R$^2$ is (CH$_2$)$_n$—(C$_6$H$_4$)—NCS wherein n is 0 to 6 by
a) reacting a compound of formula (IVa) or (IVb)

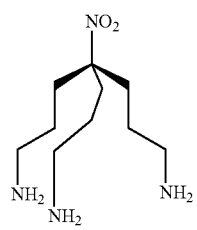

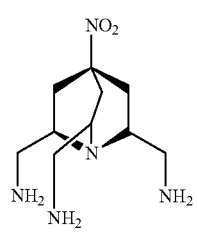

with a compound of formula (V)

$$X^Z-C(=O)Y \quad (V)$$

wherein
X$^Z$ is X as defined earlier and wherein the hydroxyl groups which are bound to X are protected; and
Y is a leaving group;
b) reducing the nitro group to obtain an amino group;
c) reacting the product obtained with a compound of formula (IX$_{A^*}$)

$$Y-C(=O)-(CH_2)_n-(C_6H_4)-NO_2 \quad (IX_{A^*})$$

wherein Y and n are as defined above;
d) reducing the nitro group to an amino group;
e) reacting the amino group with thiophosgene to give the isothiocyanate group —N=C=S; and
removing the hydroxyl protecting groups of X$^Z$.

15. Method for producing a compound of formula (II) according to claim 2 by reacting a compound of formula (I)

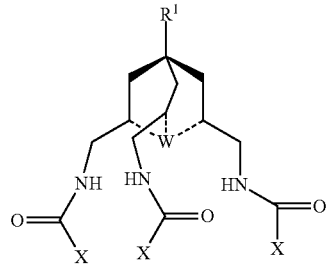
(I)

wherein
$R^1$ is H, $NO_2$, $NH_2$ or $NHC(=O)R^2$, wherein $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_n$—$(C_6H_4)$—NCS, $(CH_2)_m$—C≡CH or $(CH_2)_m$—$N_3$ wherein n is 0 to 6 and m is 1 to 6;
W and the bonds represented as dotted lines are present or absent and when present, W is N; and
X is a chelator moiety X consisting of a 6-membered aromatic or partially saturated ring system containing up to three heteroatoms selected from nitrogen and oxygen and having a hydroxyl group as a first substituent bound to a first atom in said ring system, and a hydroxyl group or an oxygen atom doubly bound to a second atom in said ring system wherein said first and second atom are adjacent atoms and wherein said first and second substituents are in ring positions such that X is capable of forming a complex with a paramagnetic metal ion; and wherein X is optionally substituted by up to three additional substituents, R, where each R is independently a hydrophilic group which renders the compound of formula (I) soluble in aqueous solutions;
with a paramagnetic metal ion.

16. Method for producing the compound of formula (I) according to claim 1 wherein $R^1$ is $NH_2$ by
a) reacting a compound of formula (IVb)

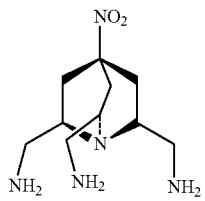
(IVb)

with a compound of formula (V)

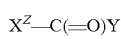    (V)

wherein
$X^Z$ is X as defined earlier and wherein the hydroxyl groups which are bound to X are protected; and
Y is a leaving group;
b) reducing the nitro group to obtain an amino group; and
c) removing the hydroxyl protecting groups of $X^Z$.

17. Method for producing the compound of formula (I) according to claim 1

(i) wherein $R^1$ is $NHC(=O)R^2$ and $R^2$ is $C_1$-$C_6$-alkyl, $C_6$-$C_{15}$-aryl, $C_7$-$C_{22}$-arylalkyl, O—$C_1$-$C_6$-alkyl, O—$C_7$-$C_{22}$-arylalkyl, $(CH_2)_m$—C≡CH or $(CH_2)_m$—$N_3$ and m is 1 to 6 by:
a) reacting a compound of formula (IVb)

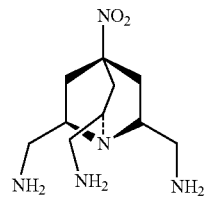
(IVb)

with a compound of formula (V)

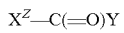    (V)

wherein
$X^Z$ is X as defined in claim 1 and wherein the hydroxyl groups which are bound to X are protected; and
Y is a leaving group;
b) reducing the nitro group to obtain an amino group;
c) reacting the product obtained with a compound of formula (IX)

    (IX)

wherein Y and $R^2$ are as defined above; and
d) removing the hydroxyl protecting groups of $X^Z$; or (ii) wherein $R^1$ is $NHC(=O)R^2$ and $R^2$ is $C_7$-$C_{22}$-arylalkyl, O—$C_1$-$C_6$-alkyl, O—$C_7$-$C_{22}$-arylalkyl, $(CH_2)_m$—C≡CH or $(CH_2)_m$—$N_3$ and m is 1 to 6 by
a) reacting a compound of formula (IVa)

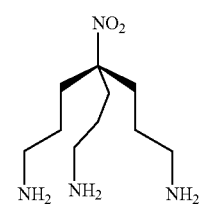
(IVa)

with a compound of formula (V)

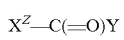    (V)

wherein
$X^Z$ is X as defined in claim 1 and wherein the hydroxyl groups which are bound to X are protected; and
Y is a leaving group;
b) reducing the nitro group to obtain an amino group;
c) reacting the product obtained with a compound of formula (IX)

    (IX)

wherein Y and $R^2$ are as defined above; and
d) removing the hydroxyl protecting groups of $X^Z$.

18. Compound of formula (I):

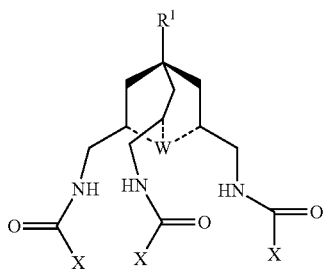

wherein
R¹ is NHC(=O)R², wherein R² is —($C_6H_4$)—NCS;
W is absent; and
X is

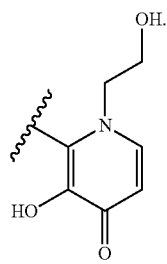 [SMILES: *c1c(O)c(=O)ccn1CCO]

19. Compound according to claim 18 further comprising a paramagnetic metal ion M to form a compound of formula (II):

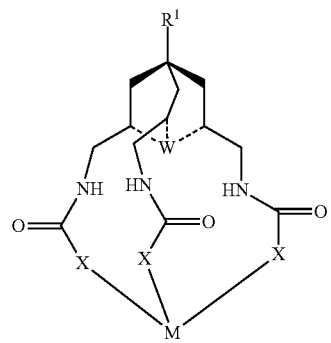

wherein
R¹, W and X are as defined in claim 18 and M is a paramagnetic metal ion.

20. Compound according to claim 19 wherein M is a paramagnetic metal ion of Mn, Fe, La, Co, Ni, Eu, Gd, Dy, Tm or Yb.

21. Compound according to claim 18 linked to another molecule via the R1-group.

22. Compound according to claim 21 wherein said another molecule is a natural or synthetic peptide, a peptidomimetic, a polypeptide, a protein, an antibody, a natural or synthetic polymer, a dendrimer, a nanoparticle or a lipophilic compound.

23. Compound according to claim 22 wherein said another molecule comprises an amino group and is selected from a polypeptide, a protein, an antibody, a natural or synthetic polymer and a dendrimer and wherein said compound of formula (I) is linked to said another molecule via a thiourea bond formed by a reaction of the R¹-group with said amino groups of said another molecule.

* * * * *